(12) United States Patent
Brennan et al.

(10) Patent No.: US 11,789,010 B2
(45) Date of Patent: Oct. 17, 2023

(54) METHODS OF TREATMENT WITH CD80 EXTRACELLULAR DOMAIN POLYPEPTIDES

(71) Applicant: Five Prime Therapeutics, Inc., South San Francisco, CA (US)

(72) Inventors: Thomas Brennan, Cupertino, CA (US); Barbara Sennino, San Francisco, CA (US); Susannah D. Barbee, San Francisco, CA (US); Ursula Jeffry, San Francisco, CA (US)

(73) Assignee: Five Prime Therapeutics, Inc., South San Francisco, CA (US)

( * ) Notice: Subject to any disclaimer, the term of this patent is extended or adjusted under 35 U.S.C. 154(b) by 971 days.

(21) Appl. No.: 16/608,911

(22) PCT Filed: Apr. 27, 2018

(86) PCT No.: PCT/US2018/029897
§ 371 (c)(1),
(2) Date: Oct. 28, 2019

(87) PCT Pub. No.: WO2018/201014
PCT Pub. Date: Nov. 1, 2018

(65) Prior Publication Data
US 2020/0182858 A1    Jun. 11, 2020

Related U.S. Application Data

(60) Provisional application No. 62/491,479, filed on Apr. 28, 2017.

(51) Int. Cl.
*G01N 33/50* (2006.01)
*G01N 15/10* (2006.01)
*G01N 15/00* (2006.01)

(52) U.S. Cl.
CPC ......... *G01N 33/5011* (2013.01); *G01N 15/10* (2013.01); *G01N 2015/0065* (2013.01);
(Continued)

(58) Field of Classification Search
CPC .............. G01N 33/5011; G01N 15/10; G01N 2015/0065; G01N 2015/1006; G01N 2333/70532; G01N 2800/52
See application file for complete search history.

(56) References Cited

U.S. PATENT DOCUMENTS

| | | |
|---|---|---|
| 5,580,756 A | 12/1996 | Linsley et al. |
| 6,071,716 A | 6/2000 | Freeman et al. |

(Continued)

FOREIGN PATENT DOCUMENTS

| | | | |
|---|---|---|---|
| EP | 2 662 383 A1 | 11/2013 | |
| EP | 2856876 B1 | 1/2018 | |

(Continued)

OTHER PUBLICATIONS

Haile et al. J Immunol 191 (5): 2829-2836 (Sep. 1, 2013).*

(Continued)

*Primary Examiner* — Gailene Gabel

(57) ABSTRACT

This application relates to use of CD80 (B7-1) extracellular domain (ECD) polypeptides and CD80-ECD fusion molecules and their use in methods of increasing the number of central memory T cells or for treatment for cancer or for use in cancer vaccine compositions.

20 Claims, 2 Drawing Sheets

Specification includes a Sequence Listing.

(52) U.S. Cl.
CPC ........... *G01N 2015/1006* (2013.01); *G01N 2333/70532* (2013.01); *G01N 2800/52* (2013.01)

(56) References Cited

U.S. PATENT DOCUMENTS

| | | | |
|---|---|---|---|
| 6,130,316 | A | 10/2000 | Freeman et al. |
| 6,218,510 | B1 | 4/2001 | Sharpe et al. |
| 6,294,660 | B1 | 9/2001 | Sharpe et al. |
| 6,319,709 | B1 | 11/2001 | Ostrand-Rosenberg et al. |
| 6,451,305 | B1 | 9/2002 | Boussiotis et al. |
| 6,491,925 | B2 | 12/2002 | Selvaraj et al. |
| 6,641,809 | B1 | 11/2003 | Linsley et al. |
| 6,653,444 | B1 | 11/2003 | Freeman et al. |
| 6,824,779 | B1 | 11/2004 | Freeman et al. |
| 6,887,471 | B1 | 5/2005 | Linsley et al. |
| 7,011,833 | B1 | 3/2006 | Sturmhoefel et al. |
| 7,064,111 | B1 | 6/2006 | Todo et al. |
| 7,070,776 | B1 | 7/2006 | Linsley et al. |
| 7,183,376 | B2 | 2/2007 | Punnonen et al. |
| 7,229,628 | B1 | 6/2007 | Allison et al. |
| 7,311,910 | B2 | 12/2007 | Linsley et al. |
| 7,619,078 | B2 | 11/2009 | Sharpe et al. |
| 7,678,890 | B2 | 3/2010 | Bosch |
| 7,794,718 | B2 * | 9/2010 | Karrer .............. A61P 37/00 424/134.1 |
| 7,968,680 | B2 | 6/2011 | Green et al. |
| 8,114,845 | B2 | 2/2012 | Langermann et al. |
| 8,268,788 | B2 | 9/2012 | Epstein et al. |
| 8,956,619 | B2 | 2/2015 | Ostrand-Rosenberg |
| 8,969,526 | B2 | 3/2015 | Baehner et al. |
| 9,220,728 | B2 | 12/2015 | Sadelain et al. |
| 9,308,236 | B2 | 4/2016 | Miller et al. |
| 9,567,642 | B2 | 2/2017 | Feldser et al. |
| 9,650,429 | B2 | 5/2017 | Ostrand-Rosenberg et al. |
| 9,834,604 | B2 | 12/2017 | Zhu et al. |
| 9,879,046 | B2 | 1/2018 | Miller et al. |
| 10,273,281 | B2 | 4/2019 | Brennan et al. |
| 2002/0147326 | A1 | 10/2002 | Chaikin et al. |
| 2004/0236091 | A1 | 11/2004 | Chicz et al. |
| 2009/0041790 | A1 | 2/2009 | Rusnak et al. |
| 2011/0044953 | A1 | 2/2011 | Allison et al. |
| 2011/0059078 | A1 | 3/2011 | Coyle et al. |
| 2011/0223188 | A1 | 9/2011 | Langermann |
| 2013/0017199 | A1 | 1/2013 | Langermann |
| 2013/0149305 | A1 | 6/2013 | Ostrand-Rosenberg et al. |
| 2014/0377253 | A1 | 12/2014 | Harding et al. |
| 2016/0024179 | A1 | 1/2016 | Warner et al. |
| 2016/0251437 | A1 | 9/2016 | Dong et al. |
| 2017/0044268 | A1 | 2/2017 | Gurney et al. |
| 2017/0145071 | A1 | 5/2017 | Brennan et al. |
| 2017/0226181 | A1 | 8/2017 | Ostrand-Rosenberg et al. |
| 2017/0274073 | A1 | 9/2017 | Grogan et al. |
| 2017/0320959 | A1 | 11/2017 | Swanson et al. |
| 2018/0044400 | A1 | 2/2018 | Kaempfer et al. |
| 2018/0117145 | A1 | 5/2018 | Selvaraj et al. |
| 2018/0244749 | A1 | 8/2018 | Swanson et al. |
| 2019/0194288 | A1 | 6/2019 | Brennan et al. |
| 2019/0202889 | A1 | 7/2019 | Brennan et al. |

FOREIGN PATENT DOCUMENTS

| | | |
|---|---|---|
| EP | 3330290 A1 | 6/2018 |
| EP | 3348571 A1 | 7/2018 |
| JP | 2011514150 A | 5/2011 |
| WO | WO-1998058965 A1 | 12/1998 |
| WO | 2003/039486 A2 | 5/2003 |
| WO | WO 2003/039486 A2 | 5/2003 |
| WO | WO 2004/029197 A2 | 4/2004 |
| WO | 2008/037080 A1 | 4/2008 |
| WO | WO-2008037080 A1 | 4/2008 |
| WO | 2008/119071 A1 | 10/2008 |
| WO | WO 2008/119071 A1 | 10/2008 |
| WO | WO 2008/121821 A1 | 10/2008 |
| WO | 2009/089149 A1 | 7/2009 |
| WO | WO 2009/089149 A1 | 7/2009 |
| WO | 2009/100309 A2 | 8/2009 |
| WO | WO-2013019906 A1 | 2/2013 |
| WO | WO 2014/151006 A2 | 9/2014 |
| WO | WO-2015200119 A1 | 12/2015 |
| WO | WO-2016007235 A1 | 1/2016 |
| WO | WO-2016161239 A1 | 10/2016 |
| WO | WO-2016168771 A2 | 10/2016 |
| WO | 2016/174200 A1 | 11/2016 |
| WO | WO 2016/174200 A1 | 11/2016 |
| WO | WO-2017019846 A1 | 2/2017 |
| WO | WO 2017/042816 A1 | 3/2017 |
| WO | WO-2017048878 A1 | 3/2017 |
| WO | WO-2017079117 A1 | 5/2017 |
| WO | WO-2017103291 A1 | 6/2017 |
| WO | WO-2017144681 A1 | 8/2017 |
| WO | WO-2017149150 A1 | 9/2017 |
| WO | WO-2017151818 A2 | 9/2017 |
| WO | WO-2017181152 A2 | 10/2017 |
| WO | WO-2017201210 A1 | 11/2017 |
| WO | WO-2017201352 A1 | 11/2017 |
| WO | WO-2018064190 A1 | 4/2018 |
| WO | WO-2018075978 A1 | 4/2018 |
| WO | 2018/201014 A1 | 11/2018 |
| WO | WO-2018201014 A1 | 11/2018 |
| WO | WO-2020047087 A1 | 3/2020 |
| WO | WO-2020172482 A1 | 8/2020 |
| WO | WO-2020227062 A1 | 11/2020 |

OTHER PUBLICATIONS

Haile et al. Soluble CD80 Restores T Cell Activation and Overcomes Tumor Cell Programmed Death Ligand-1-mediated Immune Suppression. J. Immunol 191 (5): 2829-2836 (Sep. 1, 2013).*

Liu Aihong et al. Combination B7-Fc fusion protein treatment and Treg cell depletion therapy. Clinical Cancer Research. The American Association for Cancer Research. 11 (23): 8492-8502 (Dec. 1, 2005).*

Czajkowsky, D. M. et al. "Fc-fusion proteins: new developments and future perspectives," EMBO Molecular Medicine, 4(10): 1015-1028, Wiley Online Library, United States (2012).

Haile, S.T. et al. "A Soluble Form of CD80 Enhances Antitumor Immunity by Neutralizing Programmed Death Ligand-1 and Simultaneously Providing Costimulation," Cancer Immunology Research, 2(7): 610-615, American Association of Cancer Research, United States (2014).

Haile, S.T. et al. "Soluble CD80 Restores T Cell Activation and Overcomes Tumor Cell Programmed Death Ligand-1-Mediated Immune Suppression," The Journal of Immunology, 191(5):2829-2836, American Association of Immunology United States (2013).

Ostrand-Rosenberg, S. et al., "Novel strategies for inhibiting PD-1 pathway-mediated immune suppression while simultaneously delivering activating signals to tumor-reactive T cells," Cancer Immunology, Immunotherapy, 64(10): 1287-1293, Springer Link, Germany (2015).

Sola, Ricardo J., "Giycosylation of Therapeutics Proteins: An Effective Strategy to Optimize Efficacy," Biodrugs, 24(1): 9-21, Springer, United States (2010).

Collins, M., et al., "The B7 family of immune-regulatory ligands," Genome Biology 6(6):223, BioMed Central Ltd., England, 7 pages (2005).

Felix, J., et al., "Ipilimumab reshapes T cell memory subsets in melanoma patients with clinical response," Oncoimmunology 5(7) :e1136045, Taylor & Francis Group, England, 10 pages (Feb. 18, 2016).

Findlay, L., et al., "Improved in vitro methods to predict the in vivo toxicity in man of therapeutic monoclonal antibodies including TGN1412," *Journal of Immunological Methods* 352(1-2):1-12, Elsevier B.V., Netherlands (2010).

Greaves, P. and Gribben, J.G., "The role of B7 family molecules in hematologic malignancy," *Blood* 121(5):734-744, American Society of Hematology, United States (2013).

Klebanoff, C.A., et al., "Central memory self/tumor-reactive CD8[+] T cells confer superior antitumor immunity compared with effector

(56) References Cited

OTHER PUBLICATIONS memory T cells," *Proc Natl Acad Sci USA* 102(27):9571-9576, National Academy of Sciences, United States (2005).

Mahnke, Y.D., et al., "The who's who of T-cell differentiation: Human memory T-cell subsets," *Eur J Immunol.* 43(11):2797-2809, Wiley-VCH Verlag GmbH & Co. KGaA, Germany (2013).

Ostrand-Rosenberg, S., et al., "The programmed death-1 immune-suppressive pathway: barrier to antitumor immunity," *The Journal of Immunology* 193(8):3835-3841, The American Association of Immunologists, Inc., United States (2014).

Peach, R.J., et al., "Both extracellular immunoglobin-like domains of CD80 contain residues critical for binding T cell surface receptors CTLA-4 and CD28," *The Journal of Biological Chemistry* 270(36):21181-21187, The American Society for Biochemistry and Molecular Biology, Inc., United States (1995).

Vessillier, S., et al., "Cytokine release assays for the prediction of therapeutic mAb safety in first-in man trials—Whole blood cytokine release assays are poorly predictive for TGN1412 cytokine storm," *Journal of Immunological Methods* 424:43-52, Elsevier B.V., Netherlands (May 7, 2015).

Weber, J.S., et al., "Ipilimumab increases activated T cells and enhances humoral immunity in patients with advanced melanoma," *J. Immunother.* 35(1);89-97, Lippincott Williams & Watkins, United States (2012).

Alegre, M-L., et al., "T-cell regulation by CD28 and CTLA-4," *Nature Reviews Immunology* 1:220-228, Macmillan Magazines Ltd., England (2001).

Bhatia, S., et al., "Dynamic Equilibrium of B7-1 Dimers and Monomers Differentially Affects Immunological Synapse Formation and T Cell Activation in Response to TCR/CD28 Stimulation," *The Journal of Immunology* 184(4):1821-1828, The American Association of Immunologists, Inc., United States (2010).

Dalal, S.P., et al., "Mutated CD80 may facilitate T-cell activation by inhibiting PDL1-PD1 suppression and by costimulating," *Cancer Res* 73(8 Suppl):Abstract 1264, in Proceedings of the 104th Annual Meeting of the American Association for Cancer Research, Apr. 6-10, American Association for Cancer Research, United States (2013).

Eastwood, D., et al., "Monoclonal antibody TGN1412 trial failure explained by species differences in CD28 expression on CD4$^+$ effector memory T-cells," *British Journal of Pharmacology* 161:512-526, The British Pharmacological Society, England (2010).

Freeman, G.J., et al., "B7-1 and B7-2 do not deliver identical costimulatory signals, since B7-2 but not B7-1 preferentially costimulates the initial production of IL-4," *Immunity* 2(5):523-532, Cell Press, United States (1995).

Girard, T., et al., "CD80 and CD86 IgC domains are important for quaternary structure, receptor binding and co-signaling function," *Immunology Letters* 161:65-15, Elsevier B.V., Netherlands (2014).

Gogishvili, T., et al., "Rapid Regulatory T-Cell Response Prevents Cytokine Storm in CD28 Superagonist Treated Mice," *PLoS One* 4(2):e4643, Public Library of Science, United States, 9 pages (2009).

Hünig, T., "The storm has cleared: lessons from the CD28 superagonist TGN1412 trial," *Nature Reviews Immunology* 12:317-318, Macmillan Publishers Limited, England (2012).

Kakoulidou, M., et al., "Human Soluble CD80 is Generated by Alternative Splicing, and Recombinant Soluble CD80 Binds to CD28 and CD152 Influencing T-cell Activation," *Scandinavian Journal of Immunology* 66:529-537, Blackwell Publishing Ltd., England (2007).

Lechner, M.G., et al., "Chemokines, costimulatory molecules and fusion proteins for the immunotherapy of solid tumors," *Immunotherapy* 3(11):1317-1340, Future Medicine, England (2011).

Liu, A., et al., "Combination B7-Fc Fusion Protein Treatment and Treg Cell Depletion Therapy," *Clinical Cancer Research* 11(23):8492-8502, American Association for Cancer Research, United States (2005).

Park, H-M., et al., "CD4 T-cells transduced with CD80 and 4-1BBL mRNA induce long-term CD8 T-cell responses resulting in potent antitumor effects," *Vaccine* 32:6919-6926, Elsevier Ltd., England (2014).

Pützer, B.M., et al., "Interleukin 12 and B7-1 costimulatory molecule expressed by an adenovirus vector act synergistically to facilitate tumor regression," *Proc. Natl. Acad. Sci. USA* 94:10889-10894, The National Academy of Sciences, United States (1997).

Runyon, K., et al., "The combination of chemotherapy and systemic immunotherapy with soluble B7-immunoglobulin G leads to cure of murine leukemia and lymphoma and demonstration of tumor-specific memory responses," *Blood* 97:2420-2426, The American Society of Hematology, United States (2001).

Sansom, D.M., "CD28, CTLA-4 and their ligands: who does what and to whom?" *Immunology* 101:169-177, Blackwell Science Ltd., England (2000).

Sturmhoefel, K., et al., "Potent Activity of Soluble B7-IgG Fusion Proteins in Therapy of Established Tumors and as Vaccine Adjuvant," *Cancer Research* 59:4964-4972, American Association for Cancer Research, United States (1999).

Walker, L.S.K. and Sansom, D.M., "The emerging role of CTLA4 as a cell-extrinsic regulator of T cell responses," *Nature Reviews Immunology* 11:852-863, Macmillan Publishers Limited, England (2011).

Yamaguchi, N., et al., "Induction of Tumor Regression by Administration of B7-Ig Fusion Proteins: Mediation by Type 2 CD8$^+$ T Cells and Dependence on IL-4 Production," *The Journal of Immunology* 172:1347-1354, The American Association of Immunologists, Inc., United States (2004).

Yao, S., et al., "Advances in targeting cell surface signalling molecules for immune modulation," *Nature Reviews Drug Discovery* 12:130-146, Macmillan Publishers Limited, England (2013).

Barbee, S., et al., "FPT155, a novel therapeutic CD 80-Fc fusion protein, with potent anti-tumor activity in preclinical models," presented at 2017 AACR-EORTC International Conference on Molecular Targets and Cancer Therapeutics, Oct. 30, 2017, 1 page, California, United States.

International Preliminary Report on Patentability for Application No. PCT/US2016/059838, International Bureau of WIPO, Switzerland, dated May 8, 2018, 11 pages.

Linsley, P.S., et al., "Binding of the B Cell Activation Antigen B7 to CD28 Co-stimulates T Cell Proliferation and Interleukin 2 mRNA Accumulation," *J. Exp. Med.* 173:721-730, Rockefeller University Press, United States (Mar. 1991).

Lechner, M.G., et al., "Immunogenicity of murine solid tumor models as a defining feature of in vivo behavior and response to immunotherapy," *J. Immunother.* 36(9):477-489, Wolters Kluwer, United States (2013).

Contardi, E., et al., "CTLA-4 is constitutively expressed on tumor cells and can trigger apoptosis upon ligand interaction," *Int. J. Cancer* 117:538-550, Wiley-Liss, Inc., United States (2005).

Freeman, G.J., et al., "B7, a new member of the Ig superfamily with unique expression on activated and neoplastic B cells," *J. Immunol.* 143:2714-22, American Association of Immunologists, United States (1989).

Oganesyan, V., et al., "Structural characterization of a human Fc fragment engineered for lack of effector functions," *Acta Cryst.* D64:700-04, International Union of Crystallography, Singapore (2008).

Liu, L., "Antibody Glycosylation and Its Impact on the Pharmacokinetics and Pharmacodynamics of Monoclonal Antibodies and Fc-Fusion Proteins," Journal of Pharmaceutical Sciences 104: 1866-1884, Elsevier, Netherlands (Apr. 2015).

Rajpal, A., et al., "Introduction: Antibody Structure and Function," Therapeutic Fc-Fusion Proteins 1(1):1-43, Wiley-VCH Verlag GmbH, Germany (2014).

International Preliminary Report on Patentability International Application No. PCT/US2018/029897, International Bureau of WIPO, Switzerland, dated Oct. 29, 2019, 7 pages.

International Search Report and Written Opinion for International Application No. PCT/US2018/029897, European Patent Office, Netherlands, dated Jul. 12, 2018, 11 pages.

(56) References Cited

OTHER PUBLICATIONS

Sallusto, F., "Central memory and Effector Memory T Cell Subsets; Function, Generation, and Maintenance," *Annual Review of Immunology*, 22(1): 745-763, Annual Reviews, United States (2004).
International Search Report and Written Opinion for International Application No. PCT/US2019/048560, European Patent Office, Netherlands, dated Dec. 20, 2019, 21 pages.
Horn, L.A., "Soluble CD80 Protein Delays Tumor Growth and Promotes Tumor-Infiltrating Lymphocytes," *Cancer Immunology Research*, 6(1): 59-68, (2018).
Millward, M., et al., "FPT155001: A phase Ia/Ib study of FPT15 5 (CD80FC) in patients with advanced solid tumor," Journal of Clinical Oncology, 37(8): 2019 ASCO-SITC Clinical Immuo-Oncology Symposium, (2019), 3 pages.
Anonymous, "Body Weight Information for BAB/cJ (000651)" Jackson Laboratory (JAX), available at http://www.jax.org/jax-mic-and-services/strain-data-street-pages/body-weight-chgart-000651# (Oct. 17, 2015), 2 pages.
Anonymous, "Body Weight Information for C57BL/6J (000664)," Jackson Laboratory (JAX), available at http://www.jax.org/jax-mice-and-srvices/strain-data-sheet-pages/body-eight-chart-000664 (Aug. 6, 2017), 2 pages.
International Search Report and Written opinion for International Application No. PCT/US2020/028715, International Search Authority, United States, dated Jul. 17, 2020, 13 pages.
Jones, S., et al., "Lentiviral Vector Design for Optimal T Cell Receptor Gene Expression in the Transduction of Peripheral Blood Lymphocytes and Tumor-Infiltrating Lymphocytes," Human Gene Therapy 20(6):630-640, Mary Ann Liebert, United States (2009).
Waight, J.D., et al., "Selective Fc [gamma] R Co-engagement on APCs Modulates the Activity of Therapeutic Antibodies Targeting T cell Antigens," Cancer Cell 33(6):1033-1047, Cell Press, Netherlands (Jun. 2018).
International Search Report and Written opinion for International Application No. PCT/US2020/019135, European Patent Office, Netherlands, dated Aug. 19, 2020, 18 pages.
Bruggemann, C., et al., "Predictive value of PD-L1 based on mRNA level in the treatment of stage IV melanoma with Ipilimumab," Journal of Cancer Research and Clinical Oncology 143(10):1977-1984, Springer International, Germany (Oct. 2017).
Guan, J., et al., "Programmed Death Ligand-1 (PD-L1) Expression in the Programmed Death Receptor-1 (PD-1)/PD-L1 blockade: A Key Player Against Various Cancers," Archives of Pathology & Laboratory Medicine 141(6):851-861, College of American Pathologists (Jun. 2017).
Hunier, K.A., et al., "PD-L1 Testing in Guiding Patient Selection for PD-1/PD-L1 Inhibitor Therapy in Lung Cancer," Molecular Diagnosis and Therapy 22(1):1-10, Springer, Germany (Feb. 2018).
Paz-Ares, L., et al., "CheckMate 227: A Randomized, open-label phase 3 trial of nivolumab, nivolumab plus ipilimumab, or nivolumab plus chemotherapy versus chemotherapy in chemotherapy-naïve patients with advanced non-small cell lung cancer (NSCLC)", Annals of Oncology 28(2):ii50-ii51, Elsevier, Netherlands (Apr. 2017).
Zhang, L., et al., "Programmed cell death ligand 1 (PD-L1) expression on gastric cancer and its relationship with clinicopathologic factors," Int J. Clin Exp Pathol, 8(9):11084-11091, E-century Publishing Corp, United States (2015).
International Search Report and Written Opinion for International Application No. PCT/US2020/030946, European Patent Office, Netherlands, dated Sep. 1, 2020, 21 pages.
R&D Systems, "Recombinant Human B7-1/CD80 Fc Chimera," Catalog No. 10107-B1, Revised Apr. 10, 2019, 2 pages.
Kaneko, Y., et al., "Anti-Inflammatory Activity of Immunoglobulin G Result from Fc Sialylation," Science 313:670-673, American Association for the Advancement of Science, United States (2006).
Jimenez Del Val, I., et al., "Towards the implementation of quality by design to the production of therapeutic monoclonal antibodies with desired glycosylation patterns," Biotechnology Progress 26(6):1505-1527, American Institute of Chemical Engineers, United States (Dec. 2010).

\* cited by examiner

METHODS OF TREATMENT WITH CD80 EXTRACELLULAR DOMAIN POLYPEPTIDES

CROSS REFERENCE TO RELATED APPLICATIONS

This application is a national phase entry of International Application No. PCT/US2018/029897, filed Apr. 27, 2018, which claims the priority benefit of U.S. Provisional Application No. 62/491,479, filed Apr. 28, 2017, each of which is hereby incorporated by reference herein in its entirety.

SEQUENCE LISTING

The instant application contains a sequence listing which has been submitted electronically in ASCII format and is hereby incorporated by reference in its entirety. Said ASCII copy of the sequence listing, created on Oct. 28, 2019, is named 3986_0070001_SeqListing_ST25.txt and is 60,357bytes in size.

FIELD

This application relates to CD80 (B7-1) extracellular domain (ECD) polypeptides and CD80-ECD fusion molecules and their uses in increasing central memory T cells and in methods of treatment, such as methods of treating cancer.

BACKGROUND

CD80, also known as B7-1, is one of the B7 family of membrane-bound proteins involved in immune regulation by delivering costimulatory or coinhibitory responses through their ligand binding activities. Other members of the B7 family of proteins include CD86 (B7-2), inducible costimulator ligand (ICOS-L), programmed death-1 ligand (PD-L1; B7-H1), programmed death-2 ligand (PD-L2; B7-H2), B7-H3, and B7-H4. CD80 is a transmembrane protein expressed on the surface of T cells, B cells, dendritic cells and monocytes, and binds to the receptors CD28, CTLA4 (CD152), and PD-L1. (See, e.g., M. Collins et al., *Genome Biol.* 6:223 doi:10.1186/bg-2005-6-6-223 (2005).) CD80 and CD86 and their receptors CTLA4 and CD28 operate as a costimulatory-coinhibitory system, for example, to control T cell activation, expansion, differentiation, and survival. CD80 and CD86 interaction with CD28 results in costimulatory signals that lead, for example, to activation of T cell responses. CD80, in turn, stimulates upregulation of CTLA4, which, upon binding to CD80, acts to suppress the T cell response previously triggered by CD80/CD28 interactions. This feedback loop allows for fine control of immune responses. (See, e.g., R. Peach et al., *J. Biol. Chem.* 270(36): 21181-87 (1995).)

CD80 has also been shown to interact with another B7 family member, PD-L1 with similar affinity to CD28, whereas CD86 does not interact with PD-L1. (See, e.g., P. Greaves & J. G. Gribbon, *Blood* 121(5): 734-44 (2013).) PD-L1 is one of two ligands for the programmed death-1 (PD-1) protein, which is also involved in T cell regulation. Specifically, expression of PD-1 on T cells may be induced after T cells have been activated, and binding of PD-1 to PD-L1 downregulates T cell activity by promoting T cell inactivation. (See, e.g., S. Ostrand-Rosenberg, *J. Immunol.* 193: 3835-41 (2014).) Many tumor cells express PD-L1 on their surface, potentially leading to PD-1/PD-L1 interactions and the inhibition of T cell responses against the tumor. This observation has led to the development of inhibitors of the PD-1/PD-L1 interaction as cancer therapeutics designed to stimulate natural immune responses against tumors in patients. (See Id.) Binding of CD80 to PD-L1 may serve as an alternative mechanism to block the PD-1/PD-L1 interaction and prevent inhibition of T cell responses at the site of a tumor. (See Id. at 3839.) At the same time, however, increased levels of CD80 might also be available to bind to CD28 and to induce CTLA4, thus either inducing or inhibiting T cell responses. Some soluble forms of CD80 may also function to block CTLA4 activation by blocking endogenous CD80 activity. (See Id.)

The present inventors have shown that administration of a CD80 extracellular domain (ECD) fusion polypeptide to cynomolgus monkeys induced expansion and proliferation of CD4+ and CD8+ central memory T cells in a dose dependent manner. Memory T cells are a subset of T cells that are directed to particular antigens due to previous encounters with those antigens. The presence of memory T cells may allow for a stronger and swifter immune response to the antigen if it is re-encountered in future. Central memory T cells (Tcm) are a subset of memory T cells that may retain some stem-cell-like properties. (See Y. D. Mahnke, *Eur. J. Immunol.* 43: 2797-2809 (2013).) Particular subsets of Tcm have been shown to be active against certain cancers in murine studies, for example, mounting an active tumor antigen recall response when mice are represented with previously encountered tumor antigens. (See Klebanoff et al., *PNAS* 102(27: 9571-76 (2005). Clinical studies on ipilimumab, an anti-CTLA4 antibody, have also shown alterations in T cell populations in patients who are responsive to the antibody treatment. (J. Felix et al., *Oncoimmunology* 5(7): e1136045 (2016); J. S. Weber, *J. Immunother.* 35(1): 89-97 (2012)).

SUMMARY

Provided herein are methods of determining the activity of a CD80 extracellular domain (ECD) fusion molecule in a subject comprising determining the frequency of central memory T cells and/or detecting the proliferation of central memory T cells in a sample obtained from the subject after administration of the CD80 ECD fusion molecule to the subject, wherein the CD80 ECD fusion molecule comprises a human CD80 ECD polypeptide and a human IgG1 Fc domain.

Also provided herein are methods of detecting central memory T cell frequency or proliferation in a subject comprising determining the frequency of central memory T cells and/or detecting the proliferation of central memory T cells in a sample obtained from the subject after administration of the CD80 ECD fusion molecule to the subject, wherein the CD80 ECD fusion molecule comprises a human CD80 ECD polypeptide and a human IgG1 Fc domain.

Also provided herein are methods of determining the activity of a CD80 extracellular domain (ECD) fusion molecule in a subject comprising (a) obtaining a sample from the subject after a CD80 ECD fusion molecule has been administered to the subject and (b) determining the frequency of central memory T cells and/or detecting the proliferation of central memory T cells in the sample, wherein the CD80 ECD fusion molecule comprises a human CD80 ECD polypeptide and a human IgG1 Fc domain.

Also provided herein are methods of detecting central memory T cell frequency or proliferation in a subject comprising (a) obtaining a sample from the subject after a CD80 ECD fusion molecule has been administered to the subject and (b) determining the frequency of central memory T cells and/or detecting the proliferation of central memory T cells in the sample, wherein the CD80 ECD fusion molecule comprises a human CD80 ECD polypeptide and a human IgG1 Fc domain.

In certain instances, the methods further comprise administering a CD80 ECD fusion molecule to the subject after determining the frequency of central memory T cells and/or detecting the proliferation of central memory T cells in the sample. In certain instances, the subject has cancer.

Also provided herein are methods of treating cancer in a subject comprising (a) administering to the subject a CD80 ECD fusion molecule comprising a human CD80 ECD polypeptide and a human IgG1 Fc domain; and (b) determining the frequency of central memory T cells and/or detecting the proliferation of central memory T cells in a sample obtained from the subject after the administration.

In certain instances, the methods further comprise determining the frequency of central memory T cells or detecting the proliferation of central memory T cells in a sample obtained from the subject prior to administration of the CD80 ECD fusion molecule.

In certain instances, the methods comprise determining the frequency of central memory T cells, but not detecting the proliferation of central memory T cells. In certain instances, the methods comprise detecting the proliferation of central memory T cells, but not determining the frequency of central memory T cells. In certain instances, the methods comprise determining the frequency of central memory T cells and detecting the proliferation of central memory T cells.

In certain instances, the frequency is determined using flow cytometry.

In certain instances, the proliferation is detected using flow cytometry. In certain instances, the proliferation is detected by measuring Ki67 expression. In certain instances, the proliferation is detected in a sample obtained at least 7 days after administration of the CD80 ECD fusion molecule.

Also provided herein are methods of treating cancer in a subject comprising administering to the subject a CD80 ECD fusion molecule comprising a human CD80 ECD polypeptide and a human IgG1 Fc domain, wherein (a) the frequency of memory T cells has been determined in a sample obtained from the subject prior to the administration and/or (b) the proliferation of memory T cells has been detected in a sample obtained from the subject prior to the administration.

In certain instances, the frequency of memory T cells has been determined, but the proliferation of memory T cells has not been detected. In certain instances, the proliferation of memory T cells has been detected, but the frequency of memory T cells has not been determined. In certain instances, the frequency of memory T cells has been determined and the proliferation of memory T cells has been detected.

In certain instances, the frequency has been determined using flow cytometry.

In certain instances, the proliferation has been detected using flow cytometry. In certain instances, the proliferation has been determined by measuring Ki67 expression. In certain instances, the proliferation has been detected in a sample obtained at least 7 days after administration of the CD80 ECD fusion molecule.

In certain instances, the sample is a blood sample. In certain instances, the sample is a plasma sample.

In certain instances, the central memory T cells are CD95+ and CD28+ cells. In certain instances, the central memory T cells are CD4+ central memory T cells. In certain instances, the central memory T cells are CD8+ central memory T cells. In certain instances, the central memory T cells are CD4+ and CD8+ central memory T cells.

In certain instances, the sample obtained after administration of the CD80 ECD fusion molecule is obtained at least one week after the administration. In certain instances, the sample obtained after administration of the CD80 ECD fusion molecule is obtained at least two weeks after the administration. In certain instances, the sample obtained after administration of the CD80 ECD fusion molecule is obtained at least one month after the administration.

In certain instances, the human CD80 ECD polypeptide comprises the amino acid sequence of SEQ ID NO:5. In certain instances, the human CD80 ECD polypeptide comprises the amino acid sequence of SEQ ID NO:3. In certain instances, the human CD80 ECD polypeptide comprises the amino acid sequence of SEQ ID NO:4.

In certain instances, the human IgG1 Fc domain comprises the amino acid sequence of SEQ ID NO:14.

In certain instances, the CD80 ECD fusion molecule comprises the amino acid sequence of SEQ ID NO:20. In certain instances, the CD80 ECD fusion molecule comprises the amino acid sequence of SEQ ID NO:21.

In certain instances, the CD80 ECD fusion molecule comprises 10-60 molecules of sialic acid (SA). In certain instances, the CD80 ECD fusion molecule comprises 15-40 molecules of SA. In certain instances, the CD80 ECD fusion molecule comprises 15-25 molecules of SA. In certain instances, the CD80 ECD fusion molecule comprises 15-30 molecules of SA.

In certain instances, the cancer is a solid tumor. In certain instances, the cancer is selected from the group consisting of colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer. In certain instances, the cancer is recurrent or progressive after a therapy selected from the group consisting of surgery, chemotherapy, radiation therapy, and a combination thereof.

In certain instances, the CD80 ECD fusion molecule is administered in combination with a programmed cell death 1 (PD-1)/programmed cell death ligand 1 (PD-L1) inhibitor. In certain instances, the PD-1/PD-L1 inhibitor is an antibody. In certain instances, the PD-1/PD-L1 inhibitor is an anti-PD-1 antibody. In certain instances, the anti-PD-1 antibody comprises the heavy chain and light chain CDRs of nivolumab, pidilizumab, or pembrolizumab. In certain instances, the anti-PD-1 antibody comprises the heavy chain and light chain variable regions of nivolumab, pidilizumab, or pembrolizumab. In certain instances, the anti-PD-1 antibody is nivolumab, pidilizumab, or pembrolizumab. In certain instances, the PD-1/PD-L1 inhibitor is an anti-PD-L1 antibody. In certain instances, the anti-PD-L1 antibody comprises the heavy chain and light chain CDRs of avelumab, durvalumab, atezolizumab, or BMS-936559. In certain instances, the anti-PD-L1 antibody comprises the heavy chain and light chain variable regions of avelumab, durvalumab, atezolizumab, or BMS-936559. In certain instances, the anti-PD-L1 antibody is avelumab, durvalumab, atezolizumab, or BMS-936559. In certain instances, the PD-1/PD-L1 inhibitor is a PD-1 fusion molecule. In certain instances, the fusion molecule is AMP-224. In certain instances, the PD-1/PD-L1 inhibitor is AUR-012.

In certain instances, the CD80 ECD fusion molecule is administered in combination with a cancer vaccine. In certain instances, the cancer vaccine is a personalized cancer vaccine. In certain instances, the CD80 ECD fusion molecule and the cancer vaccine are administered concurrently or sequentially.

The present disclosure encompasses methods of treating cancer in a subject in need thereof, comprising administering a CD80 extracellular domain (ECD) or CD80 ECD fusion molecule, wherein the CD80 ECD or CD80 ECD fusion molecule is administered in an amount effective to increase the number of central memory T cells in the subject. In some embodiments, the number of central memory T cells is increased for at least one week, at least two weeks, or at least one month. In some embodiments, the number of central memory T cells is determined in a blood or plasma sample of the subject. In some embodiments, the central memory T cells are CD95+ and CD28+ cells. The present disclosure also encompasses methods of treating cancer in a subject in need thereof, comprising: (a) administering to the subject a CD80 extracellular domain (ECD) or CD80 ECD fusion molecule; and (b) determining the concentration of central memory T cells in a sample obtained from the subject after administration of the CD80 ECD or CD80 ECD fusion molecule. In some embodiments, the methods further comprise determining the concentration of central memory T cells in a sample obtained from the subject prior to administration of the CD80 ECD or CD80 ECD fusion molecule. In some embodiments, the methods further comprise increasing the dose or frequency of the CD80 ECD or CD80 ECD fusion molecule administered to the subject if the concentration of central memory T cells in the sample obtained after administration is not larger than the concentration of central memory T cells in the sample obtained prior to administration. In some embodiments, the sample for determining the concentration of central memory T cells is a blood or plasma sample. In some embodiments, the central memory T cells are CD95+ and CD28+ cells.

The present disclosure also encompasses methods of increasing the number of central memory T cells in a subject in need thereof, comprising administering a CD80 extracellular domain (ECD) or CD80 ECD fusion molecule, wherein the CD80 ECD or CD80 ECD fusion molecule is administered in an amount effective to increase the number of central memory T cells in the subject. In some embodiments, the number of central memory T cells is increased for at least one week, at least two weeks, or at least one month. In some embodiments, the number of central memory T cells is determined in a blood or plasma sample of the subject. In some embodiments, the central memory T cells are CD95+ and CD28+ cells.

The present disclosure also encompasses a method of increasing the number of central memory T cells in a subject in need thereof, comprising: (a) administering to the subject a CD80 extracellular domain (ECD) or CD80 ECD fusion molecule; and (b) determining the concentration of central memory T cells in a sample obtained from the subject after administration of the CD80 ECD or CD80 ECD fusion molecule. In some embodiments, the method further comprises determining the concentration of central memory T cells in a sample obtained from the subject prior to the CD80 ECD or CD80 ECD fusion molecule administration. In some embodiments, the method further comprises increasing the dose or frequency of the CD80 ECD or CD80 ECD fusion molecule administered to the subject if the concentration of central memory T cells in the sample obtained after administration is not larger than the concentration of central memory T cells in the sample obtained prior to administration. In some embodiments, the sample for determining the concentration of central memory T cells is a blood or plasma sample. In some embodiments, the central memory T cells are CD95+ and CD28+ cells.

The present disclosure also encompasses methods of detecting central memory T cells in a subject, for example a cancer subject, the methods comprising, for example, determining the concentration of central memory T cells in a sample obtained from the subject after administration of a CD80 ECD or CD80 ECD fusion molecule to the subject.

In some of the above methods, a CD80 ECD is administered. In other methods, a CD80 ECD fusion molecule is administered. In either case, in some embodiments CD80 ECD or the CD80 ECD portion of the fusion molecule comprises an amino acid sequence selected from (a) amino acids 35 to end of SEQ ID NO:1, (b) SEQ ID NO:3, (c) SEQ ID NO:4, and (d) SEQ ID NO:5.

In some embodiments where a CD80 ECD fusion molecule is administered, the CD80 ECD fusion molecule comprises a fusion partner comprising an Fc domain. In some embodiments the Fc domain is a human IgG1 Fc domain. In some embodiments, the Fc domain comprises the amino acid sequence of SEQ ID NO:14. In some embodiments, the CD80 ECD fusion molecule comprises sequence of SEQ ID NO:20 or SEQ ID NO: 21.

In some embodiments of the above methods, the CD80 ECD comprises 10-60 mol sialic acid (SA) to mol of protein, 15-40 mol SA to mol of protein, 15-25 mol SA to mol of protein, or 15-30 mol SA to mol of protein. In some embodiments, the CD80 ECD fusion molecule comprises 10-60 mol sialic acid (SA) to mol of protein, 15-40 mol SA to mol of protein, 15-25 mol SA to mol of protein, or 15-30 mol SA to mol of protein.

In the methods herein, in some embodiments, the CD80 ECD or CD80 ECD fusion molecule is administered in combination with a programmed cell death 1 (PD-1)/programmed cell death ligand 1 (PD-L1) inhibitor. In some embodiments, the PD-1/PD-L1 inhibitor is an antibody. In some embodiments, the PD-1/PD-L1 inhibitor is an anti-PD-1 antibody. In some embodiments, the anti-PD-1 antibody comprises the heavy chain and light chain CDRs of nivolumab, pidilizumab, or pembrolizumab. In some embodiments, the anti-PD-1 antibody comprises the heavy chain and light chain variable regions of nivolumab, pidilizumab, or pembrolizumab. In some embodiments, the anti-PD-1 antibody is nivolumab, pidilizumab, or pembrolizumab. In some embodiments, the PD-1/PD-L1 inhibitor is an anti-PD-L1 antibody. In some embodiments, the anti-PD-L1 antibody comprises the heavy chain and light chain CDRs of avelumab, durvalumab, atezolizumab, or BMS-936559. In some embodiments, the anti-PD-L1 antibody comprises the heavy chain and light chain variable regions of avelumab, durvalumab, atezolizumab, or BMS-936559. In some embodiments, the anti-PD-L1 antibody is avelumab, durvalumab, atezolizumab, or BMS-936559. In some embodiments, the PD-1/PD-L1 inhibitor is a PD-1 fusion molecule. In some embodiments, the fusion molecule is AMP-224. In some embodiments, the PD-1/PD-L1 inhibitor is AUR-012.

In some embodiments of the methods herein, the subject has cancer and the subject's cancer is a solid tumor. In some embodiments, the cancer is selected from colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer. In some embodiments, the cancer is recurrent or progressive after a therapy selected from surgery, chemotherapy, radiation therapy, or a combination thereof.

In some embodiments of the above methods, the CD80 ECD or CD80 ECD fusion molecule is administered in combination with a cancer vaccine. In some embodiments, the cancer vaccine is a personalized cancer vaccine. In some embodiments, the CD80 ECD or CD80 ECD fusion molecule and the cancer vaccine are administered concurrently or sequentially.

The present disclosure also encompasses cancer vaccine compositions comprising at least one tumor-specific antigen or tumor-associated antigen and a CD80 extracellular domain (ECD) or CD80-ECD fusion molecule. In some embodiments, the vaccine compositions further comprise autologous immune cells from a subject to be treated with the vaccine. In some such embodiments, the autologous immune cells comprise antigen-presenting cells.

It is to be understood that both the foregoing general description and the following detailed description are exemplary and explanatory only and are not restrictive of the claims. The section headings used herein are for organizational purposes only and are not to be construed as limiting the subject matter described. All references cited herein, including patent applications and publications, are incorporated herein by reference in their entireties for any purpose.

DESCRIPTION OF PARTICULAR EMBODIMENTS

Definitions

Figure 1:
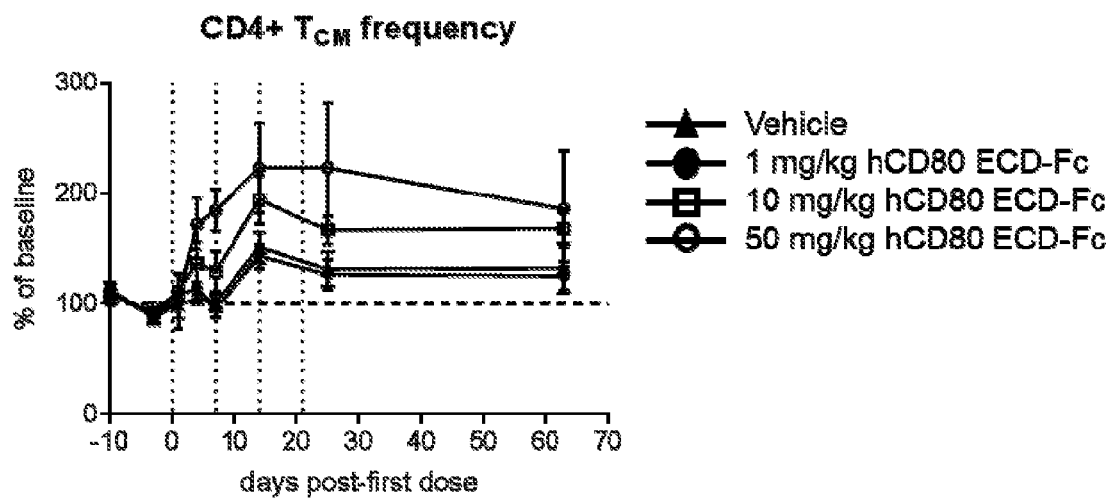
FIG. 1 shows that there is an increase in the frequency of central memory CD4+ T cells (CD4+ Tcm) in cynomolgus monkeys after treatment with human CD80 ECD-Fc (hCD80 ECD-Fc) at 10 and 50 mg/kg doses but not after treatment with a 1 mg/kg dose or with a vehicle control. Data is presented as the percentage (%) of pre-dose frequency of central memory CD4+ T cells. Dotted vertical lines represent the timing when hCD80 ECD-Fc was administered.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein that includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts that produce the proteins or errors due to PCR amplification.

A "fusion molecule" as used herein refers to a molecule composed of two or more different molecules that do not occur together in nature being covalently or noncovalently joined to form a new molecule. For example, fusion molecules may be comprised of a polypeptide and a polymer such as PEG, or of two different polypeptides. A "fusion protein" refers to a fusion molecule composed of two or more polypeptides that do not occur in a single molecule in nature.

A "CD80 extracellular domain" or "CD80 ECD" refers to an extracellular domain polypeptide of human CD80, including natural and engineered variants thereof. A "CD80 ECD fusion molecule" refers to a molecule comprising a CD80 ECD and a fusion partner such as an Fc domain, albumin, or PEG. The fusion partner may be covalently attached, for example, to the N- or C-terminal of the CD80 ECD or at an internal location.

As used herein, "central memory T cells" or "Tcm" refers to T cells, including CD4+ or CD8+ T cells, that are identified as CD95+ and CD28+, CD95+ and CD27+ or as CD95+, CD28+, and CD27+.

The terms "programmed cell death protein 1" and abbreviations "PD-1" and "PD1" refer to the full-length, mature human PD-1 protein, which is an immunoinhibitory receptor belonging to the CD28 family.

The terms "programmed cell death 1 ligand 1" and "PD-L1" (PD-L1; B7 homolog-1; B7-H1; or CD274) and "Programmed Death Ligand-2" (PD-L2; B7-DC; or CD273) are two cell surface glycoprotein ligands for PD-1 that downregulate T-cell activation and cytokine secretion upon binding to PD-1. The term "PD-L1" as used herein refers to full-length, mature, human PD-L1 unless specifically noted otherwise.

The term "immune stimulating agent" as used herein refers to a molecule that stimulates the immune system by either acting as an agonist of an immune-stimulatory molecule, including a co-stimulatory molecule, or acting as an antagonist of an immune inhibitory molecule, including a co-inhibitory molecule. An immune stimulating agent may be a biologic, such as an antibody or antibody fragment, other protein, or vaccine, or may be a small molecule drug. An "immune stimulatory molecule" includes a receptor or ligand that acts to enhance, stimulate, induce, or otherwise "turn-on" an immune response. Immune stimulatory molecules as defined herein include co-stimulatory molecules. An "immune inhibitory molecule" includes a receptor or ligand that acts to reduce, inhibit, suppress, or otherwise "turn-off" an immune response. Immune inhibitory molecules as defined herein include co-inhibitory molecules. Such immune stimulatory and immune inhibitory molecules may be, for example, receptors or ligands found on immune cells such as a T cells, or found on cells involved in innate immunity such as NK cells.

The term "PD-1/PD-L1 inhibitor" refers to a moiety that disrupts the PD-1/PD-L1 signaling pathway. In some embodiments, the inhibitor inhibits the PD-1/PD-L1 signaling pathway by binding to PD-1 and/or PD-L1. In some embodiments, the inhibitor also binds to PD-L2. In some embodiments, a PD-1/PD-L1 inhibitor blocks binding of PD-1 to PD-L1 and/or PD-L2. Nonlimiting exemplary PD-1/PD-L1 inhibitors include antibodies that bind to PD-1; antibodies that bind to PD-L1; fusion proteins, such as AMP-224; and polypeptides, such as AUR-012.

The term "antibody that inhibits PD-1" refers to an antibody that binds to PD-1 or binds to PD-L1 and thereby inhibits PD-1 and/or PD-L1 signaling. In some embodiments, an antibody that inhibits PD-1 binds to PD-1 and blocks binding of PD-L1 and/or PD-L2 to PD-1. In some embodiments, an antibody that inhibits PD-1 binds to PD-L1 and blocks binding of PD-1 to PD-L1. An antibody that inhibits PD-1 that binds to PD-L1 may be referred to as an anti-PD-L1 antibody. An antibody that inhibits PD-1 that binds to PD-1 may be referred to as an anti-PD-1 antibody.

With reference to CD80 ECDs and CD80 ECD fusion molecules, the term "blocks binding of" a ligand, and grammatical variants thereof, refers to the ability to inhibit an interaction between CD80 and a CD80 ligand, such as CD28, CTLA4, or PD-L1. Such inhibition may occur through any mechanism, including by the CD80 ECDs or CD80 ECD fusion molecules competing for binding with CD80 ligands.

With reference to anti-PD-1 antibodies and PD-1 fusion molecules or peptides the term "blocks binding of" a ligand, such as PD-L1, and grammatical variants thereof, are used to refer to the ability to inhibit the interaction between PD-1 and a PD-1 ligand, such as PD-L1. Such inhibition may occur through any mechanism, including direct interference with ligand binding, e.g., because of overlapping binding sites on PD-1, and/or conformational changes in PD-1 induced by the antibody that alter ligand affinity, etc., or, in the case of a PD-1 fusion molecule or peptide, by competing for binding with a PD-1 ligand.

"Affinity" or "binding affinity" refers to the strength of the sum total of noncovalent interactions between a single binding site of a molecule (e.g., a polypeptide) and its binding partner (e.g., a ligand). In some embodiments, "binding affinity" refers to intrinsic binding affinity, which reflects a 1:1 interaction between members of a binding pair (e.g., polypeptide and ligand). The affinity of a molecule X for its partner Y can generally be represented by the dissociation constant ($K_d$).

The term "antibody" as used herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term antibody includes, but is not limited to, fragments that are capable of binding antigen, such as Fv, single-chain Fv (scFv), Fab, Fab', and (Fab')$_2$. The term antibody also includes, but is not limited to, chimeric antibodies, humanized antibodies, and antibodies of various species such as mouse, human, cynomolgus monkey, etc.

In some embodiments, an antibody comprises a heavy chain variable region and a light chain variable region. In some embodiments, an antibody comprises at least one heavy chain comprising a heavy chain variable region and at least a portion of a heavy chain constant region, and at least one light chain comprising a light chain variable region and at least a portion of a light chain constant region. In some embodiments, an antibody comprises two heavy chains, wherein each heavy chain comprises a heavy chain variable region and at least a portion of a heavy chain constant region, and two light chains, wherein each light chain comprises a light chain variable region and at least a portion of a light chain constant region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some such embodiments, the heavy chain is the region of the antibody that comprises the three heavy chain CDRs and the light chain in the region of the antibody that comprises the three light chain CDRs.

The term "heavy chain variable region" refers to a region comprising heavy chain HVR1, framework (FR) 2, HVR2, FR3, and HVR3. In some embodiments, a heavy chain variable region also comprises at least a portion of an FR1 and/or at least a portion of an FR4.

The term "heavy chain constant region" refers to a region comprising at least three heavy chain constant domains, $C_H1$, $C_H2$, and $C_H3$. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an c constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain variable region" refers to a region comprising light chain HVR1, framework (FR) 2, HVR2, FR3, and HVR3. In some embodiments, a light chain variable region also comprises an FR1 and/or an FR4.

The term "light chain constant region" refers to a region comprising a light chain constant domain, $C_L$. Nonlimiting exemplary light chain constant regions include λ and κ.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" refers to each of the regions of an antibody variable domain which are hypervariable in sequence and/or form structurally defined loops ("hypervariable loops"). Generally, native four-chain antibodies comprise six HVRs; three in the $V_H$ (H1, H2, H3), and three in the $V_L$ (L1, L2, L3). HVRs generally comprise amino acid residues from the hypervariable loops and/or from the "complementarity determining regions" ("CDRs"), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991)). The terms hypervariable regions (HVRs) and complementarity determining regions (CDRs) both refer to portions of the variable region that form the antigen binding regions.

A "chimeric antibody" as used herein refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, a chimeric antibody comprises at least one rat variable region and at least one mouse constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is a Fab, an scFv, a (Fab')$_2$, etc.

A "human antibody" as used herein refers to antibodies produced in humans, antibodies produced in non-human animals that comprise human immunoglobulin genes, such as XenoMouse®, and antibodies selected using in vitro methods, such as phage display, wherein the antibody repertoire is based on a human immunoglobulin sequences.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

The term "isolated" as used herein refers to a molecule that has been separated from at least some of the components with which it is typically found in nature. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated" so long as that polynucleotide is not found in that vector in nature.

The term "reduce" or "reduces" when applied to a parameter such as tumor volume means to lower the level of that parameter in an observable, measurable way. In some embodiments, the reduction may be statistically significant compared to an alternative treatment or control.

The term "increase" or "expand" when applied to a parameter such as a type of cell, such as a type of T cell, means to increase in concentration (i.e., to expand or proliferate in number within a certain area such as within a tumor sample or within a volume of blood or plasma). In some embodiments, the expansion may be statistically significant compared to an alternative treatment or control.

The terms "subject" and "patient" are used interchangeably herein to refer to a human. In some embodiments, methods of treating other mammals, including, but not limited to, rodents, simians, felines, canines, equines, bovines, porcines, ovines, caprines, mammalian laboratory animals, mammalian farm animals, mammalian sport animals, and mammalian pets, are also provided.

The terms "resistant" or "nonresponsive" when used in the context of treatment with a therapeutic agent, means that the subject shows decreased response or lack of response to a standard dose of the therapeutic agent, relative to the subject's response to the standard dose of the therapeutic agent in the past, or relative to the expected response of a similar subject with a similar disorder to the standard dose of the therapeutic agent. Thus, in some embodiments, a subject may be resistant to therapeutic agent although the subject has not previously been given the therapeutic agent, or the subject may develop resistance to the therapeutic agent after having responded to the agent on one or more previous occasions.

The term "sample," as used herein, refers to a composition that is obtained or derived from a subject that contains a cellular and/or other molecular entity that is to be characterized, quantitated, and/or identified, for example based on physical, biochemical, chemical and/or physiological characteristics. An exemplary sample is a tissue sample.

The term "tissue sample" refers to a collection of similar cells obtained from a tissue of a subject. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, synovial fluid, or interstitial fluid; cells from any time in gestation or development of the subject. In some embodiments, a tissue sample is a synovial biopsy tissue sample and/or a synovial fluid sample. In some embodiments, a tissue sample is a synovial fluid sample. The tissue sample may also be primary or cultured cells or cell lines. Optionally, the tissue sample is obtained from a disease tissue/organ. The tissue sample may contain compounds that are not naturally intermixed with the tissue in nature such as preservatives, anticoagulants, buffers, fixatives, nutrients, antibiotics, or the like. A "control sample" or "control tissue", as used herein, refers to a sample, cell, or tissue obtained from a source known, or believed, not to be afflicted with the disease for which the subject is being treated.

For the purposes herein a "section" of a tissue sample means a part or piece of a tissue sample, such as a thin slice of tissue or cells cut from a solid tissue sample.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells (i.e. "solid tumors") or may be hematologic (e.g. lymphomic or leukemic) cancer cells. The term "cancer growth" is used herein to refer to proliferation or growth by a cell or cells that comprise a cancer that leads to a corresponding increase in the size or extent of the cancer.

Examples of cancer include but are not limited to, carcinoma, lymphoma, blastoma, sarcoma, and leukemia. More particular nonlimiting examples of such cancers include squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

"Treatment," as used herein, refers to therapeutic treatment, for example, wherein the object is to reduce in severity or slow progression of the targeted pathologic condition or disorder as well as, for example, wherein the object is to inhibit recurrence of the condition or disorder. In certain embodiments, the term "treatment" covers any administration or application of a therapeutic for disease in a patient, and includes inhibiting or slowing the disease or progression of the disease; partially or fully relieving the disease, for example, by causing regression, or restoring or repairing a lost, missing, or defective function; stimulating an inefficient process; or causing the disease plateau to have reduced severity. The term "treatment" also includes reducing the severity of any phenotypic characteristic and/or reducing the incidence, degree, or likelihood of that characteristic. Those in need of treatment include those already with the disorder as well as those at risk of recurrence of the disorder or those in whom a recurrence of the disorder is to be prevented or slowed down.

The term "efficacy" as used herein may be determined from one or more parameters such as survival or disease-free survival over a period of time such as 1 year, 5 years, or 10 years, as well as parameters such as the reduction in growth of one or more tumors in a subject. Pharmacokinetic parameters such as bioavailability and underlying parameters such as clearance rate may also impact efficacy. Thus, an "enhanced efficacy" (i.e. an improvement in efficacy) may be due to improved pharmacokinetic parameters as well as improved potency, and may be measured by comparing clearance rates and tumor growth in test animals or in human subjects, as well as parameters such as survival, rate of recurrence, or disease-free survival.

The term "effective amount" or "therapeutically effective amount" refers to an amount of a drug effective to treat a disease or disorder in a subject. In certain embodiments, an effective amount refers to an amount effective, at dosages and for periods of time necessary, to achieve the desired therapeutic or prophylactic result. A therapeutically effective amount of a CD80 ECD or CD80 ECD fusion molecule may vary according to factors such as the disease state, age, sex, and weight of the individual, and the ability of the drug to elicit a desired response in the individual. A therapeutically effective amount encompasses an amount in which any toxic or detrimental effects of the drug are outweighed by the therapeutically beneficial effects. In some embodiments, the expression "effective amount" refers to an amount of the drug that is effective for treating the cancer.

Administration "in combination with" one or more further therapeutic agents, such as an immune stimulating agent or cancer vaccine, includes simultaneous (concurrent) and consecutive (sequential) administration in any order.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. For example, if the therapeutic agent is to be administered orally, the carrier may be a gel capsule. If the therapeutic agent is to be administered subcutaneously, the carrier ideally is not irritable to the skin and does not cause injection site reaction.

The term "antigen" is used to denote a chemical compound such as a polypeptide that is specifically recognized by an antibody. As used herein, a "tumor-specific antigen" refers to an antigen only expressed in significant amounts by tumor cells, such as a mutant polypeptide antigen corresponding to a protein that is mutated in tumor cells. As used herein, a "tumor-associated antigen" refers to an antigen corresponding to a polypeptide that is overexpressed by tumor cells and that may also be expressed by normal cells of the same or different tissue.

The term "cancer vaccine" as used herein refers to a treatment composition that is administered to promote a specific immune response against tumor antigens. In some embodiments, the cancer vaccine may comprise tumor-specific and/or tumor-associated antigens or cells presenting tumor-specific and/or tumor associated antigens in order to promote an immune response against those antigens. Such a vaccine composition may also comprise other agents that promote an immune response such as immune stimulating agents.

The term "personalized cancer vaccine" or "personalized vaccine" refers to a cancer vaccine that comprises cells or antigens taken from the patient to be treated and optionally expanded or amplified ex vivo prior to reintroduction to the patient. For example, a personalized cancer vaccine may include tumor-specific antigens from the patient or may include immune cells or other hematopoietic cells that have been taken from the patient and allowed to proliferate ex vivo.

Exemplary CD80 Extracellular Domain and Extracellular Domain Fusion Molecules

Methods of cancer treatment with CD80 ECD or CD80 ECD fusion molecules are provided herein, as are cancer vaccines comprising CD80 ECD or CD80 ECD fusion molecules. CD80 ECDs, for example, may comprise the ECDs of human CD80 isoform 1, isoform 2, and isoform 3 (see SEQ ID NOs: 1-3). In some embodiments, CD80 ECDs and may comprise the amino acid sequence of SEQ ID NO:5.

CD80 ECD fusion molecules may comprise fusion partners such as polymers, polypeptides, lipophilic moieties, and succinyl groups. Exemplary polypeptide fusion partners include, but are not limited to, serum albumin and an IgG Fc domain. Further exemplary polymer fusion partners include, but are not limited to, polyethylene glycol, including polyethylene glycols having branched and/or linear chains. The amino acid sequences of certain exemplary Fc domains are shown in SEQ ID NOs: 9-16 herein.

In certain embodiments, the CD80 ECD or CD80 ECD fusion molecule lacks a signal peptide. In certain embodiments, the CD80 ECD or CD80 ECD fusion molecule includes at least one signal peptide, which may be selected from a native CD80 signal peptide (SEQ ID NO: 7 or amino acids 1-34 of SEQ ID NO:1) and/or a heterologous signal peptide.

In the case of a CD80 ECD fusion molecule, the fusion partner may be linked to either the amino-terminus or the carboxy-terminus of the polypeptide. In certain embodiments, the polypeptide and the fusion partner are covalently linked. If the fusion partner is also a polypeptide ("the fusion partner polypeptide"), the polypeptide and the fusion partner polypeptide may be part of a continuous amino acid sequence. In such cases, the polypeptide and the fusion partner polypeptide may be translated as a single polypeptide from a coding sequence that encodes both the polypeptide and the fusion partner polypeptide. In some such cases, the two polypeptides are directly linked in sequence such that the N-terminal of one polypeptide immediately follows the C-terminal of the other with no intervening amino acids. In other cases, a linker peptide sequence is inserted in between the two polypeptides, such as a GS linker sequence. In certain embodiments, a CD80 ECD and the fusion partner are covalently linked through other means, such as, for example, a chemical linkage other than a peptide bond. In certain embodiments, the polypeptide and the fusion partner are noncovalently linked. In certain such embodiments, they may be linked, for example, using binding pairs. Exemplary binding pairs include, but are not limited to, biotin and avidin or streptavidin, an antibody and its antigen, etc.

In some embodiments, the CD80 ECD fusion molecule comprises the sequence of SEQ ID NO: 20 or 21.

CD80 ECD fusion molecules may, depending on how they are produced, have different levels of particular glycosylation modifications. For example, a CD80 ECD fusion molecule may have different concentrations of sialic acid residues in relation to the concentration of the CD80 ECD protein. In some embodiments, a higher sialic acid content may have a longer clearance time in the body and thus an increased overall bioavailability.

In order to produce CD80 ECD fusion molecules with various levels of sialylation, CD80 ECD fusion molecules prepared from cell culture may be fractionated using anion exchange chromatography, for example. In some cases, CD80 ECD fusion molecules may be subjected to one or more initial purification processes prior to fractionation. Pooled fractions may be further analyzed using a 4,5-Methylenedioxy-1,2-phenylenediamine dihydrochloride (DMB)-high performance liquid chromatography (HPLC) based sialic acid assay in order to determine sialic acid content.

In some embodiments, the sialic acid content of the CD80 ECD fusion molecule is from 10 to 60 mol sialic acid (SA) to mol protein. In some embodiments, the sialic acid content of the CD80 ECD fusion molecule is from 15 to 60 mol SA to mol protein. For example, in some embodiments, the SA content is 10-40 mol SA/mol protein, such as 15-30 mol SA/mol protein, such as 15-25 mol SA/mol protein, such as 20-40 mol SA/mol protein, such as 20-30 mol SA/mol protein, such as 30-40 mol SA/mol protein, such as 10, 15, 20, 25, 30, 35, or 40 mol SA/mol protein. In some embodiments, the SA content is at least 15 mol SA/mol protein, such as at least 20 mol SA/mol protein, at least 25 mol SA/mol protein, at least 30 mol SA/mol protein, at least 35 mol SA/mol protein, or at least 40 mol SA/mol protein. In some such embodiments, the fusion partner is an Fc domain, such as a human IgG1, IgG2, or IgG4 Fc domain.

In some embodiments, the SA content of the CD80 ECD fusion molecule is increased or is maintained at a relatively high level in comparison to current CD80 ECD fusion molecules. In some embodiments, an increase in SA content, such as by 5, 10, 15, 20, 30, 40 or 50 mol SA to mol of CD80 ECD protein, may lead to an enhanced efficacy in at least one mouse syngeneic or xenograft tumor model. For example, in some embodiments, tumor growth in a mouse tumor model may be further reduced by at least 5%, 10%, 20%, 30%, 40%, 50%, 60%, 70%, 80%, 90%, 95%, or 98% when there is an increase in SA content, such as by 5, 10, 15, 20, 30, 40 or 50 mol SA to mol of CD80 ECD protein.

For example, in some embodiments, a CD80 ECD Fc fusion molecule, such as a fusion molecule comprising a human IgG1 Fc domain comprising between 10 and 60 mol SA/mol protein is capable of at least 80%, such as at least 90%, such as at least 95%, such as at least 98% tumor cell growth inhibition in at least one mouse syngeneic or xenograft cancer model over a period of at least ten days or at least two weeks or at least three weeks, such as ten days to two weeks or two to three weeks following inoculation with tumor cells. In some such embodiments, the molecule comprises at least 15 mol SA/mol protein, such as at least 20 mol SA/mol protein, or a range from 15-30, 15-25, or 20-30 mol SA/mol protein. In some embodiments, the mouse model is a CT26, MC38, or B16 mouse tumor model. In some embodiments, the mice are given one to three doses of the molecule at 0.3 to 3.0 mg/kg, such as at 0.3 to 0.6 mg/kg, for example over a period of one week, once tumors have reached a minimum volume. In some embodiments, the Fc domain comprises the amino acid sequence of SEQ ID NO:14. In some embodiments, the CD80 ECD fusion molecule comprises the sequence of SEQ ID NO: 20 or 21.

In some embodiments, the CD80 ECD Fc fusion molecule reduces growth of CT26 tumor cells in mice over a period of at least ten days or at least two weeks or at least three weeks, such as ten days to two weeks or two to three weeks, after inoculation by a greater degree than a CD80 ECD Fc fusion protein with the identical amino acid sequence but a lower level of SA per mol of protein. In some embodiments, the CD80 ECD Fc fusion molecule reduces growth of CT26 tumors in mice over a period of at least ten days or at least two weeks, such as over ten days to two weeks or two to three weeks, after inoculation by a greater degree than an anti-CTLA4 antibody, such as anti-CTLA4 antibody clone 9D9. In some such embodiments, the CD80 ECD Fc molecule is dosed one to three times at 0.3 mg/kg, 0.6 mg/kg, or 3.0 mg/kg while the anti-CTLA4 antibody is dosed the same number of times at 1.5 or 10 mg/kg. In some such embodiments, the model is a CT26, MC38, or B16 murine tumor model.

Exemplary Fc Domain Fusion Partners

In some embodiments, the CD80 ECD fusion molecule has an Fc domain as fusion partner. In some embodiments, the Fc domain is derived from human IgG1, IgG2, IgG3, or IgG4. In some embodiments, the Fc domain has a wild-type sequence, such as a wild-type human IgG1 or IgG2 (e.g. IgG2a) sequence. In other embodiments, the Fc domain is either a natural or engineered variant. In some embodiments, an Fc domain is chosen that has altered interactions of the Fc with one or more Fc gamma receptors. In some embodiments, an Fc domain is chosen that has altered interactions of the Fc with one or more complement factors. In some embodiments, an Fc domain is chosen that has altered interactions of the Fc with one or more Fc gamma receptors and that has altered interactions with one or more complement factors.

In some embodiments, the Fc domain comprises at least one point mutation as described in WO 2014/144960. In some embodiments, the Fc domain is a human Fc domain with a substitution at one or more of positions E233, L234, L235, P238, D265, N297, A327, P329, or P331 (wherein the numbering of these positions is according to the EU index as in Kabat). In some embodiments, the Fc domain is a human Fc domain with a mutation at L234, L235, and/or P331. In some embodiments, the Fc domain is a human Fc domain with the substitutions L234F, L235E, and P331S. (See, e.g., SEQ ID NO:12.) In some embodiments, the Fc domain has an amino acid substitution at position N297. (See, e.g., SEQ ID NO: 13.) In some embodiments, the Fc domain comprises a C237S mutation. (See, e.g., SEQ ID NO: 9.)

In some embodiments, a mutated Fc fusion partner causes the CD80 ECD Fc fusion molecule to have altered interactions with one or more Fc gamma receptors compared to those of a CD80 ECD fusion molecule with the same amino acid sequence except for the Fc domain mutations. In some embodiment, the Fc has reduced affinity for Fc gamma receptors such as one or more of FcRN, RI, RIIA, RIIB, and RIII compared to a wild-type Fc domain. In some embodiments, the Fc has reduced affinity for all of FcRN, RI, RIIA, RIIB, and RIII compared to a wild-type Fc domain.

In some embodiments, a mutated Fc fusion partner causes the CD80 ECD Fc fusion molecule to have altered interactions with at one or more complement factors such as C1, C2, C3, C4, and their cleavage products, such as C4a, C4b, C2a, C2b, C3a, and C3b. In some embodiments, a mutated Fc fusion partner causes the CD80 ECD Fc fusion molecule to have altered interactions with one or more complement factors compared to those of a CD80 ECD fusion molecule with the same amino acid sequence except for the Fc domain mutations.

In some embodiments the CD80 ECD and the fusion partner, such as an Fc fusion partner, are directly linked such that the N- or C-terminal amino acid of the Fc immediately precedes or follows the N- or C-terminal amino acid of the CD80 ECD sequence. (See, e.g., SEQ ID NOs: 20 and 21.) In other embodiments, the CD80 ECD and fusion partner are joined by a linker molecule, such as by a linker peptide sequence, such as by a GS linker sequence.

CD80 ECD and CD80 ECD fusion molecules may also include the CD80 and CD80 ECD fusion molecules described, for example, in U.S. patent application Ser. No. 15/340,238, filed Nov. 1, 2016, which is incorporated herein by reference in its entirety.

Central Memory T Cells and T Cell Subsets

Several different types or subsets of T cells may be found in the body. Naïve T cells (Tn) having a specific epitope specificity are produced in the thymus. After naïve T cells encounter the appropriate antigen, they proliferate and differentiate into effector cells, which can travel to sites of inflammation. Following an infection or a vaccination, for example, the vast majority of the effector T cells die by apoptosis, while a small fraction develop into various types of memory T cells, which can remain in bodily tissues, and which can help guard against re-infection with the antigen. Multiple types or subsets of memory T cells may persist in the body. These have been identified in part due to their different combinations of surface protein markers. As noted earlier, "central memory T cells" or "Tcm" are T cells, including CD4+ or CD8+ T cells, which are identified as CD95+ and CD28+, CD95+ and CD27+ or as CD95+, CD28+, and CD27+. Such cells encompass at least three further memory T cell subtypes. First, Tcm as defined herein encompass a type of memory T cell that may appear early in differentiation from naïve T cells (Tn cells) called a stem central memory T cell (Tscm). Tscm overexpress CD95 and are also CD45RO−, CCR7+, and CD28+. Second, Tcm includes cells that are CD45RO+, CCR7+, CD95+, and CD28+, which may be referred to elsewhere as Tcm or a component of Tcm. Third, Tcm may include a subset of memory T cells called transitional memory T cells (Ttm), which are CD45+, CCR7−, CD95+, and CD28+. All of these Tscm, Tcm, and Ttm cells are CD95+/CD28+ and thus, are within the scope of Tcm as used herein. Furthermore, in some embodiments, Tcm may also express CD62L.

Tscm cells may be precursors of some or all of the other types of memory T cells, including other Tcm, Ttm, as well as effector memory T cells (Tem), and terminal effector memory cells (Tte). Tem are CD45RO+, CCR7−, CD28−, and CD95+ and Tte are CD45RO−, CCR7−, CD28−, and CD95+. Moreover, Tem do not express CD62L.

Tcm may be found in tissues such as lymph nodes, spleen, and blood, while Tem, in contrast, may be found initially in peripheral nonlymphoid tissues such as lung, liver, and intestine, but can migrate to other tissues such as lymph nodes.

In some embodiments, the number or concentration of Tcm is determined, for example, either prior to or following administration of CD80 ECD or CD80 ECD fusion molecule to the patient.

Therapeutic Compositions and Methods

Methods of Increasing Central Memory T Cells and Methods of Treating Cancer

The present disclosure provides, for example, methods of increasing the number of central memory T cells (Tcm) in a patient in need thereof, comprising administering a human CD80 extracellular domain (ECD) or CD80 ECD fusion molecule, wherein the CD80 ECD or CD80 ECD fusion molecule is administered in an amount effective to increase the number of Tem in the patient. In some embodiments, the number of Tem in the patient is determined by analyzing the number or concentration of Tem in a blood or plasma sample from the patient or in a sample of diseased tissue from the patient, such as a tumor sample. In such embodiments, an increase or decrease in the number of Tem in the patient is based on whether the number or concentration of Tem in the tested sample is increased or decreased relative to that of a sample taken at a different time-point, such as prior to administration. In some embodiments, the number of central memory T cells in the patient is increased for at least one week after administration, such as for at least two weeks or for at least one month after administration.

The present disclosure also provides methods of increasing the number of Tem cells in a patient in need thereof, comprising: administering to the patient a human CD80 extracellular domain (ECD) or CD80 ECD fusion molecule, and determining the concentration of central memory T cells in a sample from the patient after administration. In some embodiments, the concentration of central memory T cells is also determined in a sample obtained prior to administration. In some embodiments, the concentrations of Tcm in the pre- and post-administration samples are compared to determine if the Tcm concentration has increased after administration. In some embodiments, if the concentration of Tcm has not increased, more CD80 ECD or CD80 ECD fusion molecule is administered. In some embodiments the Tcm concentration is measured in a blood or plasma sample while in other embodiments, it is measured in a sample of diseased tissue, such as a tumor sample. In some embodiments, the concentration of central memory T cells in samples from the patient remains increased compared to the pre-administration level for at least one week after administration, such as for at least two weeks or for at least one month after administration.

The present disclosure provides, for example, methods of treating cancer in a patient in need thereof, comprising administering a human CD80 extracellular domain (ECD) or CD80 ECD fusion molecule, wherein the CD80 ECD or CD80 ECD fusion molecule is administered in an amount effective to increase the number of central memory T cells (Tcm) in the patient. In some embodiments, the number of Tcm in the patient is determined by analyzing the number or concentration of Tcm in a blood or plasma sample from the patient or in a tumor sample from the patient. In such embodiments, an increase or decrease in the number of Tcm in the patient is based on whether the number or concentration of Tcm in the tested sample is increased or decreased relative to that of a sample taken at a different time-point, such as prior to administration. In some embodiments, the number of central memory T cells in the patient is increased for at least one week after administration, such as for at least two weeks or for at least one month after administration.

The present disclosure also provides methods of treating cancer in a patient in need thereof, comprising: administering to the subject a human CD80 extracellular domain (ECD) or CD80 ECD fusion molecule, and determining the concentration of central memory T cells in the sample after administration. In some embodiments, the concentration of central memory T cells is also determined in a sample obtained prior to administration. The present disclosure also encompasses methods of detecting central memory T cells in a subject, for example in a cancer subject, the methods comprising, for example, determining the concentration of central memory T cells in a sample obtained from the subject before and/or after administration of a CD80 ECD or CD80 ECD fusion molecule to the subject. In some embodiments, the concentrations of Tcm in the pre- and post-administration samples are compared to determine if the Tcm concentration has increased after administration. In some embodiments, if the concentration of Tcm has not increased, more CD80 ECD or CD80 ECD fusion molecule is administered. In some embodiments the Tcm concentration is measured in a blood or plasma sample while in other embodiments, it is measured in a tumor sample. In some embodiments, the concentration of central memory T cells in samples from the patient remains increased compared to the pre-administration level for at least one week after administration, such as for at least two weeks or for at least one month after administration.

In some embodiments, the cancer may be benign (also referred to as a benign tumor), pre-malignant, or malignant. In some embodiments, the cancer may be a non-hematologic or "solid tumor" form of cancer, or alternatively, the cancer may comprise hematologic (e.g. lymphoma or leukemia) cancer cells. In some embodiments, the CD80 ECD or CD80 ECD fusion molecule is effective to reduce cancer growth in a human or animal subject, or in a mouse syngeneic or xenograft model for the cancer being treated. In some embodiments, the CD80 ECD or CD80 ECD fusion molecule is effective to reduce tumor volume, such as in a mouse syngeneic or xenograft model for the cancer being treated. Changes in tumor volume may be measured, for example, by monitoring the size (e.g. diameter) and optionally the shape of a primary tumor in the animal. Tumor growth may be measured, for example, as changes in tumor volume over time.

Examples of particular cancers that may be treated include but are not limited to, carcinoma, lymphoma, blastoma, sarcoma, and leukemia. More particular nonlimiting examples of such cancers include but are not limited to squamous cell cancer, small-cell lung cancer, pituitary cancer, esophageal cancer, astrocytoma, soft tissue sarcoma, non-small cell lung cancer (including squamous cell non-small cell lung cancer), adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cell carcinoma, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer (including squamous cell carcinoma of the head and neck).

In any of the above method embodiments, the CD80 ECD or CD80 ECD fusion molecule administered to the subject may inhibit tumor growth in a mouse syngeneic xenograft cancer model over a period of 1 week, 10 days, 2 weeks, or 3 weeks, for example, by at least 10%, at least 20%, at least 30%, at least 40%, at least 50%, at least 60%, at least 70%, at least 80%, at least 90%, at least 95%, or at least 98%. In some embodiments, the CD80 ECD fusion molecule may inhibit tumor growth in a CT26 mouse xenograft tumor model by at least 10%, at least 20%, at least 30%, at least 40%, at least 50%, at least 60%, at least 70%, at least 80%, at least 90%, at least 95%, or at least 98% at two weeks or at three weeks post-inoculation. In some such cases, the fusion molecule may be dosed one to three times at 0.3 to 3 mg/kg, such as at 0.3 to 0.6 mg/kg. In any of the above method embodiments, administration of the CD80 ECD or CD80 ECD fusion molecule administered to the subject may reduce the volume of at least one tumor in a human or animal subject by at least 10%, at least 20%, at least 30%, at least 40%, at least 50%, at least 60%, at least 70%, at least 80%, at least 90%, at least 95%, or at least 98%, for example, over a period of one month, two months, three months, six months, or one year. In some cases, the CD80 ECD Fc fusion molecule may be capable of resulting in complete tumor regression in a mouse tumor model such as a CT26 model, for example in a significant portion of tested mice, such as at least 40%, or at least 50% of mice.

In any of these methods, the CD80 ECD or CD80 ECD fusion molecule may be a CD80 ECD Fc comprising 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21. Such CD80 ECD and CD80 ECD fusion molecules are described, for example, in U.S. patent application Ser. No. 15/340,238, filed Nov. 1, 2016, which is incorporated herein by reference in its entirety.

Combination Treatments with Immune Stimulating Agents Including PD-1/PD-L1 Inhibitors In some embodiments, the CD80 ECD or CD80 ECD fusion molecule is administered in the methods herein in combination with an effective amount of at least one immune stimulating agent. Immune stimulating agents may include, for example, a small molecule drug or a biologic. Examples of biologic immune stimulating agents include, but are not limited to, antibodies, antibody fragments, fragments of receptor or ligand polypeptides, for example that block receptor-ligand binding, vaccines and cytokines.

In some embodiments, the at least one immune stimulating agent comprises an agonist of an immune stimulatory molecule, including a co-stimulatory molecule, while in some embodiments, the at least one immune stimulating agent comprises an antagonist of an immune inhibitory molecule, including a co-inhibitory molecule. In some embodiments, the at least one immune stimulating agent comprises an agonist of an immune-stimulatory molecule, including a co-stimulatory molecule, found on immune cells, such as T cells. In some embodiments, the at least one immune stimulating agent comprises an antagonist of an immune inhibitory molecule, including a co-inhibitory molecule, found on immune cells, such as T cells. In some embodiments, the at least one immune stimulating agent comprises an agonist of an immune stimulatory molecule, including a co-stimulatory molecule, found on cells involved in innate immunity, such as NK cells. In some embodiments, the at least one immune stimulating agent comprises an antagonist of an immune inhibitory molecule, including a co-inhibitory molecule, found on cells involved in innate immunity, such as NK cells. In some embodiments, the combination enhances the antigen-specific T cell response in the treated subject and/or enhances the innate immunity response in the subject. In some embodiments, the combination results in an improved anti-tumor response in an animal cancer model, such as a syngeneic or xenograft model, compared to administration of either the CD80 ECD or CD80 ECD fusion molecule or immune stimulating agent alone. In some embodiments, the combination results in a synergistic response in an animal cancer model, such as a syngeneic or xenograft model, compared to administration of either the CD80 ECD or CD80 ECD fusion molecule or immune stimulating agent alone.

In any of the above combination therapy method embodiments, the combination of the CD80 ECD or CD80 ECD fusion molecule with the immune stimulating agent, such as a PD-1/PD-L1 inhibitor, that is administered to the subject may inhibit tumor growth in a mouse syngeneic or xenograft cancer model over a period of 1 week, 10 days, 2 weeks, or 3 weeks, for example, by at least 10%, at least 20%, at least 30%, at least 40%, at least 50%, at least 60%, at least 70%, at least 80%, at least 90%, at least 95%, or at least 98%. In any of the above combination therapy method embodiments, the combination of the CD80 ECD or CD80 ECD fusion molecule with the immune stimulating agent, such as a PD-1/PD-L1 inhibitor, that is administered to the subject may reduce the volume of at least one tumor in the subject or in an animal model by at least 10%, at least 20%, at least 30%, at least 40%, at least 50%, at least 60%, at least 70%, at least 80%, at least 90%, or at least 95%, for example, over a period of one month, two months, three months, six months, or one year.

In any of the combination therapy methods, the CD80 ECD or CD80 ECD fusion molecule may be a CD80 ECD Fc comprising 10-60 mol SA to mol of CD80 ECD Fc protein, such as 15-60 mol SA/mol protein. In some embodiments, the content is 10-40 mol SA/mol protein, such as 15-40 mol SA/mol protein, such as 20-40 mol SA/mol protein, 20-30 mol SA/mol protein, 15-25 mol SA/mol protein, 15-30 mol SA to mol of protein, or 30-40 mol SA/mol protein. In some embodiments, the SA content is at least 15, such as at least 20, at least 25, at least 30, at least 35, or at least 40 mol SA/mol protein. In some embodiments, the SA content is 15, 20, 25, 30, 35, or 40 mol SA/mol protein. In some embodiments, the Fc domain is a human IgG1, IgG2, or IgG4 Fc domain. In some embodiments, the Fc domain comprises the amino acid sequence of SEQ ID NO:14. In some embodiments, the fusion molecule comprises the amino acid sequence of SEQ ID NO:20 or 21. In any of the combination treatment embodiments herein, the CD80 ECD or CD80 ECD fusion molecule may be a molecule described in US Application No. 15,340,238, filed Nov. 1, 2016, for example.

In certain embodiments, an immune stimulating agent targets a stimulatory or inhibitory molecule that is a member of the immunoglobulin super family (IgSF). For example, an immune stimulating agent may be an agent that targets (or binds specifically to) another member of the B7 family of polypeptides. An immune stimulating agent may be an agent that targets a member of the TNF family of membrane bound ligands or a co-stimulatory or co-inhibitory receptor binding specifically to a member of the TNF family. Exemplary TNF and TNFR family members that may be targeted by immune stimulating agents include CD40 and CD40L, OX-40, OX-40L, GITR, GITRL, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY and NGFR.

In some embodiments, an immune stimulating agent may comprise (i) an antagonist of a protein that inhibits T cell activation (e.g., immune checkpoint inhibitor) such as CTLA4 (e.g. an anti-CTLA4 antibody, e.g. YERVOY (ipilimumab) or tremelimumab), LAG-3 (e.g. an anti-LAG-3 antibody, for example, BMS-986016 (WO10/19570, WO14/08218), or IMP-731 or IMP-321 (WO08/132601, WO09/44273), TIM3, Galectin 9, CEACAM-1, BTLA, CD69, Galectin-1, TIGIT, CD113, GPR56, VISTA, B7-H3 (e.g. MGA271 (WO11/109400)), B7-H4, 2B4, CD48, GARP, PD1H, LAIR1, TIM-1, TIM-4, and ILT4 and/or may comprise (ii) an agonist of a protein that stimulates T cell activation such as B7-2, CD28, 4-1BB (CD137) (e.g. a CD137 agonist antibody such as urelumab or PF-05082566 (WO12/32433)), 4-1BBL, ICOS, ICOS-L, OX40 (e.g. an OX40 agonist antibody, for example, MEDI-6383, MEDI-6469 or MOXR0916 (RG7888; WO06/029879)), OX40L, GITRL, CD70, CD27 (e.g. an agonistic CD27 antibody such as varlilumab (CDX-1127)), CD40, CD40L, DR3, and CD28H. In some embodiments, the agonist of a protein that stimulates T cell activation is an antibody.

In some embodiments, an immune stimulating agent may comprise an agent that inhibits or is an antagonist of a cytokine that inhibits T cell activation (e.g., IL-6, IL-10, TGF-β, VEGF, and other immunosuppressive cytokines), and in some embodiments an immune stimulating agent may comprise an agent that is an agonist of a cytokine, such as IL-2, IL-7, IL-12, IL-15, IL-21 and IFNα (e.g., the cytokine itself) that stimulates T cell activation. TGF-β inhibitors include, e.g., GC1008, LY2157299, TEW7197 and IMC-TR1. In some embodiments, immune stimulating agents may comprise an antagonist of a chemokine, such as CXCR2 (e.g., MK-7123), CXCR4 (e.g. AMD3100), CCR2, or CCR4 (mogamulizumab).

In some embodiments, the at least one immune stimulating agent comprises a Toll-like receptor agonist, e.g., a TLR2/4 agonist (e.g., *Bacillus* Calmette-Guerin); a TLR7 agonist (e.g., Hiltonol or Imiquimod); a TLR7/8 agonist (e.g., Resiquimod); or a TLR9 agonist (e.g., CpG7909).

In some embodiments, immune stimulating agents may include antagonists of inhibitory receptors on NK cells or agonists of activating receptors on NK cells. In some embodiments, the at least one immune stimulating agent is an antagonist of KIR, e.g. the antibody lirilumab.

In some embodiments, an immune stimulating agent may comprise an anti-GITR agonist antibody such as TRX-518 (WO06/105021, WO09/009116), MK-4166 (WO11/028683) or the GITR antibody disclosed in WO2015/031667.

Immune stimulating agents may also include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Immune stimulating agents may also include certain vaccines such as mesothelin-targeting vaccines or attenuated listeria cancer vaccines, such as CRS-207.

Immune stimulating agents may also comprise agents that deplete or block Treg cells, such as agents that specifically bind to CD25.

Immune stimulating agents may also comprise agents that inhibit a metabolic enzyme such as indoleamine dioxygenase (IDO), dioxigenase, arginase, or nitric oxide synthetase. IDO antagonists include, for example, INCB-024360 (WO2006/122150, WO07/75598, WO08/36653, WO08/36642), indoximod, NLG-919 (WO09/73620, WO09/1156652, WO11/56652, WO12/142237) and F001287.

Immune stimulating agents may also comprise agents that inhibit the formation of adenosine or inhibit the adenosine A2A receptor.

Immune stimulating agents may also comprise agents that reverse/prevent T cell anergy or exhaustion and agents that trigger an innate immune activation and/or inflammation at a tumor site.

The treatment combinations can also be further combined in a combinatorial approach that targets multiple elements of the immune pathway, such as one or more of the following: at least one agent that enhances tumor antigen presentation (e.g., dendritic cell vaccine, GM-CSF secreting cellular vaccines, CpG oligonucleotides, imiquimod); at least one agent that inhibits negative immune regulation e.g., by inhibiting CTLA4 pathway and/or depleting or blocking Treg or other immune suppressing cells; a therapy that stimulates positive immune regulation, e.g., with agonists that stimulate the CD-137 and/or OX-40 pathway and/or stimulate T cell effector function; at least one agent that increases systemically the frequency of anti-tumor T cells; a therapy that depletes or inhibits Tregs, such as Tregs in the tumor, e.g., using an antagonist of CD25 (e.g., daclizumab) or by ex vivo anti-CD25 bead depletion; at least one agent that impacts the function of suppressor myeloid cells in the tumor; a therapy that enhances immunogenicity of tumor cells (e.g., anthracyclines); adoptive T cell or NK cell transfer including genetically modified cells, e.g., cells modified by chimeric antigen receptors (CAR-T therapy); at least one agent that inhibits a metabolic enzyme such as indoleamine dioxigenase (IDO), dioxigenase, arginase or nitric oxide synthetase; at least one agent that reverses/prevents T cell anergy or exhaustion; a therapy that triggers an innate immune activation and/or inflammation at a tumor site; administration of immune stimulatory cytokines or blocking of immuno repressive cytokines.

For example, the at least one immune stimulating agent may comprise one or more agonistic agents that ligate positive costimulatory receptors; one or more antagonists (blocking agents) that attenuate signaling through inhibitory receptors, such as antagonists that overcome distinct immune suppressive pathways within the tumor microenvironment; one or more agents that increase systemically the frequency of anti-tumor immune cells, such as T cells, deplete or inhibit Tregs (e.g., by inhibiting CD25); one or more agents that inhibit metabolic enzymes such as IDO; one or more agents that reverse/prevent T cell anergy or exhaustion; and one or more agents that trigger innate immune activation and/or inflammation at tumor sites.

In some embodiments, the CD80 ECD or CD80 ECD fusion molecule is administered in combination with an effective amount of a PD-1/PD-L1 inhibitor.

PD-1/PD-L1 Inhibitors

PD-1/PD-L1 inhibitors include antibodies, fusion proteins, and peptides. A nonlimiting exemplary fusion protein that is a PD-1/PD-L1 inhibitor is AMP-224 (Amplimmune, GlaxoSmithKline). A nonlimiting exemplary polypeptide that is a PD-1/PD-L1 inhibitor is AUR-012. Other exemplary PD-1/PD-L1 inhibitors include antibodies that inhibit PD-1, such as anti-PD-1 antibodies and anti-PD-L1 antibodies. Such antibodies may be humanized antibodies, chimeric antibodies, mouse antibodies, and human antibodies.

In some embodiments, the PD-1/PD-L1 inhibitor is an anti-PD-L1 antibody, such as atezolizumab (Tecentriq®), durvalumab, avelumab, or BMS-936559.

In some embodiments, the PD-1/PD-L1 inhibitor is an anti-PD-1 antibody. In one embodiment, the anti-PD-1 antibody is nivolumab. Nivolumab (also known as Opdivo®; formerly designated 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56). In some embodiments, nivolumab is administered at a dose of 3 mg/kg every 2 weeks or at a flat dose of 240 mg every 2 weeks. In another embodiment, the anti-PD-1 antibody is pembrolizumab. Pembrolizumab (also known as Keytruda®, formerly lambrolizumab, and MK-3475) is a humanized monoclonal IgG4 anti-PD-1 antibody. Pembrolizumab is described, for example, in U.S. Pat. No. 8,900,587; see also www (dot) cancer (dot) gov (slash) drugdictionary?cdrid=695789 (last accessed: Mar. 27, 2017). Pembrolizumab has been approved by the FDA for the treatment of relapsed or refractory melanoma. For example, a flat dose of the anti-PD-1 antibody pembrolizumab can be 200 mg. In some embodiments, pembrolizumab may be administered at 200 mg every 3 weeks. In other embodiments, the anti-PD-1 Ab is MEDI0608 (formerly AMP-514). MEDI0608 is described, for example, in U.S. Pat. No. 8,609,089, B2 or in www (dot) cancer (dot) gov (slash) drugdictionary?cdrid=756047 (last accessed Mar. 27, 2017). In some embodiments, the anti-PD-1 antibody is Pidilizumab (CT-011), which is a humanized monoclonal antibody. Pidilizumab is described in U.S. Pat. No. 8,686,119 B2 or WO 2013/014668 A1.

Additional Combination Therapies

CD80 ECDs or CD80 ECD fusion molecules may also be provided before, substantially contemporaneous with, or after other modes of treatment, for example, surgery, chemotherapy, radiation therapy, or the administration of another biologic.

For treatment of cancer for example, CD80 ECDs or CD80 ECD fusion molecules may be administered in conjunction with one or more additional anti-cancer agents, such as the chemotherapeutic agent, growth inhibitory agent, anti-angiogenesis agent and/or anti-neoplastic composition. Nonlimiting examples of chemotherapeutic agent, growth inhibitory agent, anti-angiogenesis agent, anti-cancer agent and anti-neoplastic composition that can be used in combination with the antibodies of the present invention are provided in the following definitions.

A "chemotherapeutic agent" is a chemical compound useful in the treatment of cancer. Examples of chemotherapeutic agents include, but are not limited to, alkylating agents such as thiotepa and Cytoxan® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, *Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, Adriamycin® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), Abraxane® Cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometlhylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including Nolvadex® tamoxifen), raloxifene, droloxifene, 4-hydroxytamoxifen, trioxifene, keoxifene, LY117018, onapristone, and Fareston® toremifene; aromatase inhibitors that inhibit the enzyme aromatase, which regulates estrogen production in the adrenal glands, such as, for example, 4(5)-imidazoles, aminoglutethimide, Megase® megestrol acetate, Aromasin® exemestane, formestanie, fadrozole, Rivisor® vorozole, Femara® letrozole, and Arimidex® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., Angiozyme® ribozyme) and a HER2 expression inhibitor; vaccines such as gene therapy vaccines, for example, Allovectin® vaccine, Leuvectin® vaccine, and Vaxid® vaccine; Proleukin® rIL-2; Lurtotecan® topoisomerase 1 inhibitor; Abarelix® rmRH; and pharmaceutically acceptable salts, acids or derivatives of any of the above.

An "anti-angiogenesis agent" or "angiogenesis inhibitor" refers to a small molecular weight substance, a polynucleotide (including, e.g., an inhibitory RNA (RNAi or siRNA)), a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent, e.g., antibodies to VEGF-A (e.g., bevacizumab (Avastin®) or to the VEGF-A receptor (e.g., KDR receptor or Flt-1 receptor), anti-PDGFR inhibitors such as Gleevec® (Imatinib Mesylate), small molecules that block VEGF receptor signaling (e.g., PTK787/ZK2284, SU6668, Sutent®/SU11248 (sunitinib malate), AMG706, or those described in, e.g., international patent application WO 2004/113304). Anti-angiogensis agents also include native angiogenesis inhibitors, e.g., angiostatin, endostatin, etc. See, e.g., Klagsbrun and D'Amore (1991) *Annu. Rev. Physiol.* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known anti-angiogenic factors); and, Sato (2003) *Int. J. Clin. Oncol.* 8:200-206 (e.g., Table 1 listing anti-angiogenic agents used in clinical trials).

A "growth inhibitory agent" as used herein refers to a compound or composition that inhibits growth of a cell (such as a cell expressing VEGF) either in vitro or in vivo. Thus, the growth inhibitory agent may be one that significantly reduces the percentage of cells (such as a cell expressing VEGF) in S phase. Examples of growth inhibitory agents include, but are not limited to, agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W. B. Saunders, Philadelphia, 1995), e.g., p. 13. The taxanes (paclitaxel and docetaxel) are anticancer drugs both derived from the yew tree. Docetaxel (Taxotere®, Rhone-Poulenc Rorer), derived from the European yew, is a semi-synthetic analogue of paclitaxel (Taxol®, Bristol-Myers Squibb). Paclitaxel and docetaxel promote the assembly of microtubules from tubulin dimers and stabilize microtubules by preventing depolymerization, which results in the inhibition of mitosis in cells.

The term "anti-neoplastic composition" refers to a composition useful in treating cancer comprising at least one active therapeutic agent. Examples of therapeutic agents include, but are not limited to, e.g., chemotherapeutic agents, growth inhibitory agents, cytotoxic agents, agents used in radiation therapy, anti-angiogenesis agents, other cancer immunotherapeutic agents aside from PD-1/PD-L1 inhibitors, apoptotic agents, anti-tubulin agents, and otheragents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib)(Tarceva®), platelet derived growth factor inhibitors (e.g., Gleevec® (Imatinib Mesylate)), a COX-2 inhibitor (e.g., celecoxib), interferons, CTLA-4 inhibitors (e.g., anti-CTLA antibody ipilimumab (YERVOY®)), PD-L2 inhibitors (e.g., anti-PD-L2 antibodies), TIM3 inhibitors (e.g., anti-TIM3 antibodies), cytokines, antagonists (e.g., neutralizing antibodies) that bind to one or more of the following targets ErbB2, ErbB3, ErbB4, PDGFR-beta, BlyS, APRIL, BCMA, PD-L2, CTLA-4, TIM3, or VEGF receptor(s), TRAIL/Apo2, and other bioactive and organic chemical agents, etc. Combinations thereof are also included in the invention.

Routes of Administration and Carriers

In various embodiments, polypeptides and fusion molecules may be administered in vivo by various routes, including, but not limited to, oral, intra-arterial, parenteral, intranasal, intravenous, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. A nucleic acid molecule encoding a polypeptide may be coated onto gold microparticles and delivered intradermally by a particle bombardment device, or "gene gun," as described in the literature (see, e.g., Tang et al., *Nature* 356:152-154 (1992)). The appropriate formulation and route of administration may be selected according to the intended application.

In various embodiments, polypeptide-comprising compositions are provided in formulations with a wide variety of pharmaceutically acceptable carriers (see, e.g., Gennaro, *Remington: The Science and Practice of Pharmacy with Facts and Comparisons: Drugfacts Plus*, 20$^{th}$ ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In various embodiments, compositions comprising polypeptides and fusion molecules may be formulated for injection, including subcutaneous administration, by dissolving, suspending, or emulsifying them in an aqueous or nonaqueous solvent, such as vegetable or other oils, synthetic aliphatic acid glycerides, esters of higher aliphatic acids, or propylene glycol; and if desired, with conventional additives such as solubilizers, isotonic agents, suspending agents, emulsifying agents, stabilizers and preservatives. In various embodiments, the compositions may be formulated for inhalation, for example, using pressurized acceptable propellants such as dichlorodifluoromethane, propane, nitrogen, and the like. The compositions may also be formulated, in various embodiments, into sustained release microcapsules, such as with biodegradable or non-biodegradable polymers. A non-limiting exemplary biodegradable formulation includes poly lactic acid-glycolic acid polymer. A non-limiting exemplary non-biodegradable formulation includes a polyglycerin fatty acid ester. Certain methods of making such formulations are described, for example, in EP 1 125 584 A1.

Pharmaceutical packs and kits comprising one or more containers, each containing one or more doses of a polypeptide or combination of polypeptides are also provided. In some embodiments, a unit dosage is provided wherein the unit dosage contains a predetermined amount of a composition comprising a polypeptide or combination of polypeptides, with or without one or more additional agents. In some embodiments, such a unit dosage is supplied in a single-use prefilled syringe for injection. In various embodiments, the composition contained in the unit dosage may comprise saline, sucrose, or the like; a buffer, such as phosphate, or the like; and/or be formulated within a stable and effective pH range. Alternatively, in some embodiments, the composition may be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition of the invention comprises heparin and/or a proteoglycan.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated.

CD80 ECD and ECD Fusion Molecules in Combination with or as Components of Cancer Vaccines The present disclosure also includes methods of administering a CD80 ECD or CD80 ECD fusion molecule in combination with a cancer vaccine composition comprising at least one tumor-specific or tumor-associated antigen. The disclosure also provides cancer vaccine compositions comprising a CD80 ECD or CD80 ECD fusion molecule and at least one tumor-specific or tumor-associated antigen. In either situation (whether the CD80 ECD or CD80 ECD fusion molecule is administered separately or is a component of a cancer vaccine), the cancer vaccine may be a personalized cancer vaccine.

In some embodiments, the tumor-specific or tumor-associated antigen may be an antigen commonly found associated with the tumor. In some embodiments, the tumor-specific or tumor-associated antigen may be an antigen found on the particular patient's tumor and that has been, for example, produced or amplified ex vivo and then reintroduced as a vaccine. In some embodiments, the antigen may be provided on the surface of immune cells such as antigen-presenting cells, which are then administered to the patient.

The present disclosure also provides for a CD80 ECD or CD80 ECD fusion protein as a component of a cancer vaccine composition. For example, a cancer vaccine composition may comprise a tumor-specific or tumor-associated antigen in combination with a CD80 ECD or CD80 ECD fusion protein.

In such vaccine compositions and methods, the CD80 ECD or CD80 ECD fusion protein may be capable of altering the memory T cell subsets in the patient administered the vaccine.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Effect of CD80 ECD-Fc Administration on CD4+ and CD8+ Central Memory T Cells in Cynomolgus Monkeys A study was conducted in monkey (*Macaca fascicularis*) naive cynomolgus using human CD80 ECD-Fc, consisting of the extracellular domain (ECD) of human CD80 linked to the Fc domain of wild-type human IgG1. Human CD80 ECD-Fc was tested at 1 mg/kg, 10 mg/kg, and 50 mg/kg administered weekly for 4 weeks.

Sixteen monkeys were administered vehicle or human CD80-ECD-Fc on day 1, 8, 15 and 22. Each experimental group was composed of 4 animals, 2 female and 2 male. One animal of each sex from each dose group was euthanized at day 26. The remaining animals were retained and observed for a post-dosing recovery period of six weeks.

Whole venous blood samples were collected at the following timepoints: two predose samples at least one week apart, 24 hours post-first dose on day 2, day 4, predose on day 8, predose on day 15 and on the days of scheduled necropsy, day 26 and day 64.

Flow cytometry analysis was performed on whole blood samples to evaluate frequency, activation, and proliferation of T cells (CD8+ T cells and CD4+ T cells), T regulatory cells (Treg), NK cells, and T cell memory subset repertoire (naïve, central memory, and effector memory).

Treatment with human CD80 ECD-Fc did not induce overt changes to the frequencies of major lymphocyte (NK cells, B cells, total CD4+ or CD8+ T cells, or Treg) in peripheral blood of cynomolgus monkeys. Human CD80

Figure 2:
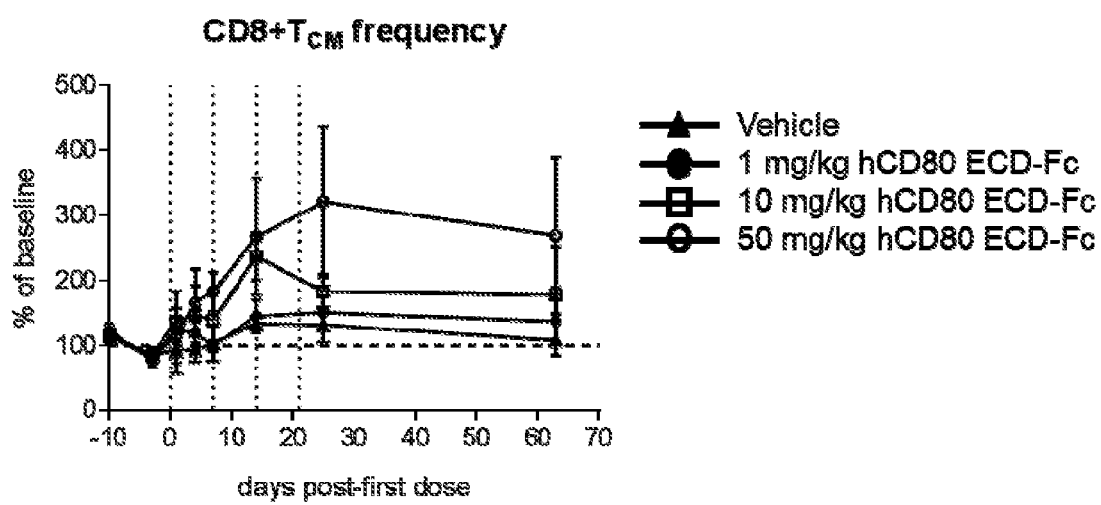
FIG. 2 shows changes in the frequency of central memory CD8+ T cells (CD8+ Tcm) in cynomolgus monkeys after treatment with 1, 10, or 50 mg/kg hCD80 ECD-Fc or vehicle control. Data is presented as the percentage (%) of pre-dose frequency of central memory CD8+ T cells. Dotted vertical lines represent the timing when hCD80 ECD-Fc was administered.
Figure 3:
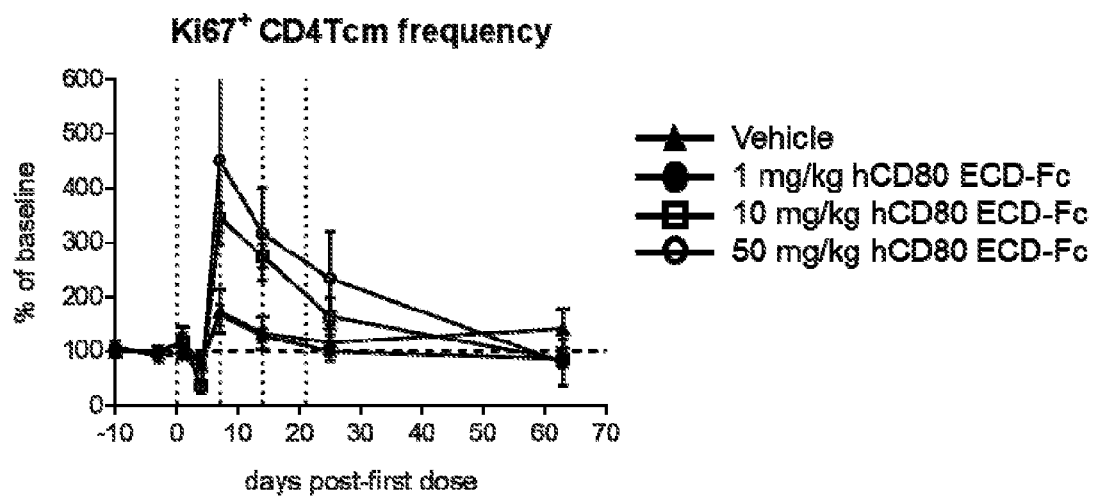
FIG. 3 shows changes in proliferating (Ki67+) central memory CD4+ T cells after treatment with 1, 10, or 50 mg/kg hCD80 ECD-Fc or vehicle control. Data is presented as the percentage (%) of average pre-dose frequency of central memory CD4+ T cells. Dotted vertical lines represent the timing when hCD80 ECD-Fc was administered. Maximum frequency of Ki67+CD4+ Tcm occurred 7 days after first dose.
Figure 4:
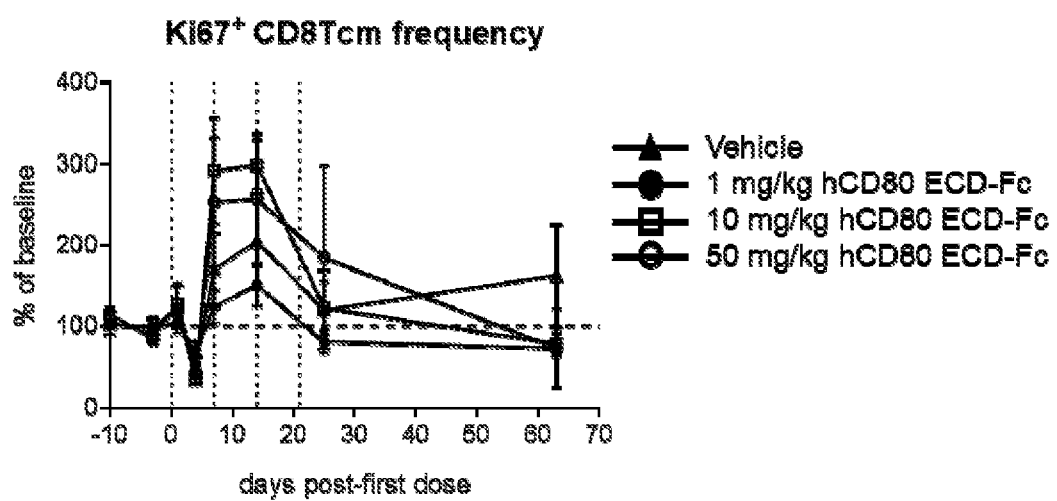
FIG. 4 shows changes in proliferating (Ki67+) central memory CD8+ T cells after treatment with 1, 10, or 50 mg/kg hCD80 ECD-Fc or vehicle control. Data is presented as the percentage (%) of average pre-dose frequency of central memory CD8+ T cells and expressed as mean value+/−standard deviation. Dotted vertical lines represent the timing when hCD80 ECD-Fc was administered. Maximum frequency of Ki67+CD8+ Tcm occurred 7 days after second dose.

ECD-Fc induced dose-dependent expansion and proliferation of central memory T cell subsets (Tcm). Expansion of central memory CD4+ and CD8+ T cells expressing CD95 and CD28 was observed in the groups dosed with 10 and 50 mg/kg but not in the group dosed with 1 mg/kg. The central memory CD4+ and CD8+ T cell populations continued to expand in frequency after each dose of human CD80 ECD-Fc and then were reduced by the end of study (FIGS. 1 and 2). The proliferation of central memory CD4+ and CD8+ T cells as measured by Ki67 expression was also increased in the groups treated with the 10 mg/kg and 50 mg/kg. Ki67 expression was maximal in CD4+ Tcm at 7 days after the first dose and in CD8+ Tcm at 7 days after the second dose; Ki67 expression returned to baseline levels by the end of the study (FIGS. 3 and 4).

TABLE OF SEQUENCES

The table below provides a listing of certain sequences referenced herein.

| SEQ. ID. NO. | Description | Sequence |
|---|---|---|
| 1 | Human CD80 precursor (with signal sequence) amino acid sequence | MGHTRRQGTSPSKCPYLNFFQLLVLAGLSHFCSG VIHVTKEVKEVATLSCGHNVSVEELAQTRIYWQ KEKKMVLTMMSGDMNIWPEYKNRTIFDITNNLS IVILALRPSDEGTYECVVLKYEKDAFKREHLAEV TLSVKADFPTPSISDFEIPTSNIRRIICSTSGGFPEPH LSWLENGEELNAINTTVSQDPETELYAVSSKLDF NMTTNHSFMCLIKYGHLRVNQTFNWNTTKQEH FPDNLLPSWAITLISVNGIFVICCLTYCFAPRCRER RRNERLRRESVRPV |
| 2 | Mouse CD80 precursor (with signal sequence) amino acid sequence | MACNCQLMQDTPLLKFPCPRLILLFVLLIRLSQ VSSDVDEQLSKSVKDKVLLPCRYNSPHEDESE DRIYWQKHDKVVLSVIAGKLKVWPEYKNRT LYDNTTYSLIILGLVLSDRGTYSCVVQKKERG TYEVKHLALVKLSIKADFSTPNITESGNPSAD TKRITCFASGGFPKPRFSWLENGRELPGINTTI SQDPESELYTISSQLDFNTTRNHTIKCLIKYGD AHVSEDFTWEKPPEDPPDSKNTLVLFGAGFG AVITVVVIVVIIKCFCKHRSCFRRNEASRETNN SLTFGPEEALAEQTVFL |
| 3 | Human CD80 Isoform 2 (without signal sequence) | VIHVTKEVKEVATLSCGHNVSVEELAQTRIY WQKEKKMVLTMMSGDMNIWPEYKNRTIFDI TNNLSIVILALRPSDEGTYECVVLKYEKDAFK REHLAEVTLSVKADFPTPSISDFEIPTSNIRRIIC STSGGFPEPHLSWLENGEELNAINTTVSQDPE TELYAVSSKLDFNMTTNHSFMCLIKYGHLRV NQTFNWNTSFAPRCRERRRNERLRRESVRPV |
| 4 | Human CD80 Isoform 3 (without signal sequence) | VIHVTKEVKEVATLSCGHNVSVEELAQTRIY WQKEKKMVLTMMSGDMNIWPEYKNRTIFDI TNNLSIVILALRPSDEGTYECVVLKYEKDAFK REHLAEVTLSVKGFAPRCRERRRNERLRRESV RPV |
| 5 | Human CD80 ECD sequence (without signal sequence) | VIHVTKEVKEVATLSCGHNVSVEELAQTRIYWQ KEKKMVLTMMSGDMNIWPEYKNRTIFDITNNLS IVILALRPSDEGTYECVVLKYEKDAFKREHLAEV TLSVKADFPTPSISDFEIPTSNIRRIICSTSGGFPEPH LSWLENGEELNAINTTVSQDPETELYAVSSKLDF NMTTNHSFMCLIKYGHLRVNQTFNWNTTKQEH FPDN |
| 6 | Mouse CD80 ECD sequence (without signal sequence) | VDEQLSKSVKDKVLLPCRYNSPHEDESEDRIY WQKHDKVVLSVIAGKLKVWPEYKNRTLYDN TTYSLIILGLVLSDRGTYSCVVQKKFRGTYEV KHLALVKLSIKADFSTPNITESGNPSADTKRIT CFASGGFPKPRFSWLENGRELPGINTTISQDP ESELYTISSQLDFNTTRNHTIKCLIKYGDAHV SEDFTWEKPPEDPPDSKN |
| 7 | Human CD80 signal sequence | MGHTRRQGTSPSKCPYLNFFQLLVLAGLSHFCSG |
| 8 | Mouse CD80 signal sequence | MACNCQLMQDTPLLKFPCPRLILLFVLLIRLSQVS SD |
| 9 | Fc C237S | EPKSSDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT |

TABLE OF SEQUENCES-continued

The table below provides a listing of certain sequences referenced herein.

| SEQ. ID. NO. | Description | Sequence |
|---|---|---|
| | | ISKAKGQPRE PQVYTLPPSRD ELTKNQVSLT CLVKGFYPSD IAVEWESNGQ PENNYKTTPP VLDSDGSFFL YSKLTVDKSR WQQGNVFSCS VMHEALHNHYTQKSLSLSPGK |
| 10 | Fc | ERKCCVECPP CPAPPVAGPS VFLFPPKPKD TLMISRTPEV TCVVVDVSHE DPEVQFNWYV DGVEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK |
| 11 | Fc | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK |
| 12 | Human IgG1 Fc L234F, L235E, P331S mutant | EPKSSDKTHTCPPCPAPEFEGGPSVFLFPPKPKDT LMISRTPEVTCVVVDVSHEDPEVKFNWYVDGVE VHNAKTKPREEQYNSTYRVVSVLTVLHQDWLN GKEYKCKVSNKALPASIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPGK |
| 13 | Human IgG1 Fc N297 mutant | EPKSSDKTHTCPPCPAPELLGGPSVFLFPPKPKDT LMISRTPEVTCVVVDVSHEDPEVKFNWYVDGVE VHNAKTKPREEQYGSTYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPGK |
| 14 | Fc human IgG1 | EPKSSDKTHTCPPCPAPELLGGPSVFLFPPKPKDT LMISRTPEVTCVVVDVSHEDPEVKFNWYVDGVE VHNAKTKPREEQYNSTYRVVSVLTVLHQDWLN GKEYKCKVSNKALPAPIEKTISKAKGQPREPQVY TLPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPGK |
| 15 | Fc human IgG3 | ELKTPLGDTTHTCPRCPEPKSCDTPPPCPRCPEPK SCDTPPPCPRCPEPKSCDTPPPCPRCPAPELLGGPS VFLFPPKPKDTLMISRTPEVTCVVVDVSHEDPEV QFKWYVDGVEVHNAKTKPREEQYNSTFRVVSV LTVLHQDWLNGKEYKCKVSNKALPAPIEKTISKT KGQPREPQVYTLPPSREEMTKNQVSLTCLVKGF YPSDIAVEWESSGQPENNYNTTPPMLDSDGSFFL YSKLTVDKSRWQQGNIFSCSVMHEALHNRFTQK SLSLSPGK |
| 16 | Fc human IgG4 | ESKYGPPCPPCPAPEFLGGPSVFLFPPKPKDTLMI SRTPEVTCVVVDVSQEDPEVQFNWYVDGVEVH NAKTKPREEQFNSTYRVVSVLTVLHQDWLNGKE YKCKVSNKGLPSSIEKTISKAKGQPREPQVYTLPP SQEEMTKNQVSLTCLVKGFYPSDIAVEWESNGQ PENNYKTTPPVLDSDGSFFLYSRLTVDKSRWQEG NVFSCSVMHEALHNHYTQKSLSLSLGK |
| 17 | Mouse CD80 ECD mouse Fc IgG2 (Fc portion underlined) | VDEQLSKSVKDKVLLPCRYNSPHEDESEDRIYW QKHDKVVLSVIAGKLKVWPEYKNRTLYDNTTY SLIILGLVLSDRGTYSCVVQKKERGTYEVKHLAL VKLSIKADFSTPNITESGNPSADTKRITCFASGGFP KPRFSWLENGRELPGINTTISQDPESELYTISSQLD FNTTRNHTIKCLIKYGDAHVSEDFTWEKPPEDPP <u>DSKNEPRGPTIKPCPPCKCPAPNLLGGPSVFIFPPK IKDVLMISLSPIVTCVVVDVSEDDPDVQISWFVN NVEVHTAQTQTHREDYNSTLRVVSALPIQHQDW</u> |

TABLE OF SEQUENCES-continued

The table below provides a listing of certain sequences referenced herein.

| SEQ. ID. NO. | Description | Sequence |
|---|---|---|
|  |  | MSGKEFKCKVNNKDLPAPIERTISKPKGSVRAPQ VYVLPPPEEEMTKKQVTLTCMVTDFMPEDIYVE WTNNGKTELNYKNTEPVLDSDGSYFMYSKLRV EKKNWVERNSYSCSVVHEGLHNHHTTKSFSRTP GK |
| 18 | Mouse CD80 ECD Human Fc IgG1 WT (Fc portion underlined) | VDEQLSKSVKDKVLLPCRYNSPHEDESEDRIYW QKHDKVVLSVIAGKLKVWPEYKNRTLYDNTTY SLIILGLVLSDRGTYSCVVQKKERGTYEVKHLAL VKLSIKADFSTPNITESGNPSADTKRITCFASGGFP KPRFSWLENGRELPGINTTISQDPESELYTISSQLD FNTTRNHTIKCLIKYGDAHVSEDFTWEKPPEDPP DSKNEPKSSDKTHTCPPCPAPELLGGPSVFLFPPK PKDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQPR EPQVYTLPPSRDELTKNQVSLTCLVKGFYPSDIA VEWESNGQPENNYKTTPPVLDSDGSFFLYSKLTV DKSRWQQGNVFSCSVMHEALHNHYTQKSLSLSP GK |
| 19 | Mouse CD80 ECD Fc IgG1 MT (234, 235, 331) (Fc portion underlined; mutants shown in bold) | VDEQLSKSVKDKVLLPCRYNSPHEDESEDRIYW QKHDKVVLSVIAGKLKVWPEYKNRTLYDNTTY SLIILGLVLSDRGTYSCVVQKKERGTYEVKHLAL VKLSIKADFSTPNITESGNPSADTKRITCFASGGFP KPRFSWLENGRELPGINTTISQDPESELYTISSQLD FNTTRNHTIKCLIKYGDAHVSEDFTWEKPPEDPP DSKNEPKSSDKTHTCPPCPAPEFEGGPSVFLFPPK PKDTLMISRTPEVTCVVVDVSHEDPEVKFNWYV DGVEVHNAKTKPREEQYNSTYRVVSVLTVLHQ DWLNGKEYKCKVSNKALPASIEKTISKAKGQPR EPQVYTLPPSRDELTKNQVSLTCLVKGFYPSDIA VEWESNGQPENNYKTTPPVLDSDGSFFLYSKLTV DKSRWQQGNVFSCSVMHEALHNHYTQKSLSLSP GK |
| 20 | Human CD80 ECD Human Fc IgG1 WT (Fc portion underlined) | VIHVTKEVKEVATLSCGHNVSVEELAQTRIYWQ KEKKMVLTMMSGDMNIWPEYKNRTIFDITNNLS IVILALRPSDEGTYECVVLKYEKDAFKREHLAEV TLSVKADFPTPSISDFEIPTSNIRRIICSTSGGFPEPH LSWLENGEELNAINTTVSQDPETELYAVSSKLDF NIVITTNHSFMCLIKYGHLRVNQTFNAVNTTKQEH FPDNEPKSSDKTHTCPPCPAPELLGGPSVFLFPPK PKDTLMISRTPEVTCVVVDVSHEDPEVKFNWYV DGVEVHNAKTKPREEQYNSTYRVVSVLTVLHQ DWLNGKEYKCKVSNKALPAPIEKTISKAKGQPR EPQVYTLPPSRDELTKNQVSLTCLVKGFYPSDIA VEWESNGQPENNYKTTPPVLDSDGSFFLYSKLTV DKSRWQQGNVFSCSVMHEALHNHYTQKSLSLSP GK |
| 21 | Human CD80 ECD Human Fc IgG1 L234F, L235E P331S MT (Fc portion underlined; mutants in bold) | VIHVTKEVKEVATLSCGHNVSVEELAQTRIYWQ KEKKMVLTMMSGDMNIWPEYKNRTIFDITNNLS IVILALRPSDEGTYECVVLKYEKDAFKREHLAEV TLSVKADFPTPSISDFEIPTSNIRRIICSTSGGFPEPH LSWLENGEELNAINTTVSQDPETELYAVSSKLDF NMTTNHSFMCLIKYGHLRVNQTFNWNTTKQEH FPDNEPKSSDKTHTCPPCPAPEFEGGPSVFLFPPK PKDTLMISRTPEVTCVVVDVSHEDPEVKFNWYV DGVEVHNAKTKPREEQYNSTYRVVSVLTVLHQ DWLNGKEYKCKVSNKALPASIEKTISKAKGQPR EPQVYTLPPSRDELTKNQVSLTCLVKGFYPSDIA VEWESNGQPENNYKTTPPVLDSDGSFFLYSKLTV DKSRWQQGNVFSCSVMHEALHNHYTQKSLSLSP GK |

TABLE OF SEQUENCES-continued

The table below provides a listing of certain sequences referenced herein.

| SEQ. ID. NO. | Description | Sequence |
|---|---|---|
| 22 | human PD-1 precursor (with signal sequence) UniProtKB/ Swiss-Prot: Q15116.3, 1 OCT. 2014 | MQIPQAPWPV VWAVLQLGWR PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 23 | human PD-1 (mature, without signal sequence) | PGWFLDSPDR PWNPPTFSPA LLVVTEGDNA TFTCSFSNTS ESFVLNWYRM SPSNQTDKLA AFPEDRSQPG QDCRFRVTQL PNGRDFHMSV VRARRNDSGT YLCGAISLAP KAQIKESLRA ELRVTERRAE VPTAHPSPSP RPAGQFQTLV VGVVGGLLGS LVLLVWVLAV ICSRAARGTI GARRTGQPLK EDPSAVPVFS VDYGELDFQW REKTPEPPVP CVPEQTEYAT IVFPSGMGTS SPARRGSADG PRSAQPLRPE DGHCSWPL |
| 24 | human PD-L1 precursor (with signal sequence) UniProtKB/ Swiss-Prot: Q9NZQ7.1, 1 OCT. 2014 | MRIFAVFIFM TYWHLLNAFT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRMMDVK KCGIQDTNSK KQSDTHLEET |
| 25 | human PD-L1 (mature, without signal sequence) | FT VTVPKDLYVV EYGSNMTIEC KFPVEKQLDL AALIVYWEME DKNIIQFVHG EEDLKVQHSS YRQRARLLKD QLSLGNAALQ ITDVKLQDAG VYRCMISYGG ADYKRITVKV NAPYNKINQR ILVVDPVTSE HELTCQAEGY PKAEVIWTSS DHQVLSGKTT TTNSKREEKL FNVTSTLRIN TTTNEIFYCT FRRLDPEENH TAELVIPELP LAHPPNERTH LVILGAILLC LGVALTFIFR LRKGRIMMDVK KCGIQDTNSK KQSDTHLEET |

What is claimed is:

1. A method of increasing central memory T cell (Tcm) frequency and/or proliferation in a subject, which method comprises administering a CD80 extracellular domain (ECD) fusion molecule to the subject in an amount effective to increase Tcm frequency and/or proliferation, wherein the CD80 ECD fusion molecule comprises a human CD80 ECD polypeptide and a human IgG1 Fc domain.

2. The method of claim 1, wherein the subject has cancer.

3. The method of claim 2, wherein the cancer is selected from the group consisting of colorectal cancer, breast cancer, gastric cancer, non-small cell lung cancer, melanoma, squamous cell carcinoma of the head and neck, ovarian cancer, pancreatic cancer, renal cell carcinoma, hepatocellular carcinoma, bladder cancer, and endometrial cancer.

4. The method of claim 2, wherein the cancer is recurrent or progressive after surgery, chemotherapy, radiation therapy, or a combination thereof.

5. The method of claim 2, wherein the CD80 ECD fusion molecule is administered in combination with a programmed cell death 1 (PD-1)/programmed cell death ligand 1 (PD-L1) inhibitor.

6. The method of claim 2, wherein the CD80 ECD fusion molecule is administered in combination with a cancer vaccine.

7. The method of claim 6, wherein the CD80 ECD fusion molecule and the cancer vaccine are administered concurrently or sequentially.

8. The method of claim 1, wherein the central memory T cells are CD95+ and CD28+cells.

9. The method of claim 8, wherein the central memory T cells are CD4+central memory T cells.

10. The method of claim 8, wherein the central memory T cells are CD8+ central memory T cells.

11. The method of claim 1, wherein increased central memory T cell proliferation is detected in a sample obtained from the subject at least 7 days after administration of the CD80 ECD fusion molecule.

12. The method of claim 11, wherein the central memory T cell proliferation is determined by measuring Ki67 expression.

13. The method of claim 11, wherein the sample is a plasma sample, blood sample, or tumor sample.

14. The method of claim 1, wherein the human CD80 ECD polypeptide comprises the amino acid sequence of SEQ ID NO:5.

15. The method of claim 1, wherein the human IgG1 Fc domain comprises the amino acid sequence of SEQ ID NO:14.

16. The method of claim 1, wherein the CD80 ECD fusion molecule comprises the amino acid sequence of SEQ ID NO:20.

17. The method of claim 1, wherein the CD80 ECD fusion molecule comprises 10-60 molecules of sialic acid (SA).

18. The method of claim 1, wherein Tcm frequency and/or proliferation is increased relative to Tem frequency and/or proliferation in the subject prior to said administering.

19. The method of claim 1, wherein the central memory T cells are CD4+central memory T cells.

20. The method of claim 1, wherein the central memory T cells are CD8+central memory T cells.

* * * * *

SEQUENCE LISTING

<160> NUMBER OF SEQ ID NOS: 25

<210> SEQ ID NO 1
<211> LENGTH: 288
<212> TYPE: PRT
<213> ORGANISM: Artificial Sequence
<220> FEATURE:
<223> OTHER INFORMATION: Human CD80 precursor (with signal sequence) amino acid sequence

<400> SEQUENCE: 1

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

```
Tyr Trp Gln Lys Glu Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 2
<211> LENGTH: 306
<212> TYPE: PRT
<213> ORGANISM: Artificial Sequence
<220> FEATURE:
<223> OTHER INFORMATION: Mouse CD80 precursor (with signal sequence)
      amino acid sequence

<400> SEQUENCE: 2

Met Ala Cys Asn Cys Gln Leu Met Gln Asp Thr Pro Leu Leu Lys Phe
 1               5                  10                  15

Pro Cys Pro Arg Leu Ile Leu Leu Phe Val Leu Leu Ile Arg Leu Ser
             20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
 65                  70                  75                  80

Ile Ala Gly Lys Leu Lys Val Trp Pro Glu Tyr Lys Asn Arg Thr Leu
                 85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140
```

```
Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Ile Val Val Ile Ile Lys Cys Phe Cys
            260                 265                 270

Lys His Arg Ser Cys Phe Arg Arg Asn Glu Ala Ser Arg Glu Thr Asn
                275                 280                 285

Asn Ser Leu Thr Phe Gly Pro Glu Glu Ala Leu Ala Glu Gln Thr Val
    290                 295                 300

Phe Leu
305

<210> SEQ ID NO 3
<211> LENGTH: 222
<212> TYPE: PRT
<213> ORGANISM: Artificial Sequence
<220> FEATURE:
<223> OTHER INFORMATION: Human CD80 Isoform 2 (without signal sequence)

<400> SEQUENCE: 3

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190
```

Gln Thr Phe Asn Trp Asn Thr Ser Phe Ala Pro Arg Cys Arg Glu Arg
        195                 200                 205

Arg Arg Asn Glu Arg Leu Arg Arg Glu Ser Val Arg Pro Val
    210                 215                 220

<210> SEQ ID NO 4
<211> LENGTH: 128
<212> TYPE: PRT
<213> ORGANISM: Artificial Sequence
<220> FEATURE:
<223> OTHER INFORMATION: Human CD80 Isoform 3 (without signal sequence)

<400> SEQUENCE: 4

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Gly Phe Ala Pro Arg Cys Arg
            100                 105                 110

Glu Arg Arg Arg Asn Glu Arg Leu Arg Arg Glu Ser Val Arg Pro Val
        115                 120                 125

<210> SEQ ID NO 5
<211> LENGTH: 208
<212> TYPE: PRT
<213> ORGANISM: Artificial Sequence
<220> FEATURE:
<223> OTHER INFORMATION: Human CD80 ECD sequence (without signal
      sequence)

<400> SEQUENCE: 5

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

```
Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 6
<211> LENGTH: 209
<212> TYPE: PRT
<213> ORGANISM: Artificial Sequence
<220> FEATURE:
<223> OTHER INFORMATION: Mouse CD80 ECD sequence (without signal
      sequence)

<400> SEQUENCE: 6

```
Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
            180                 185                 190

Glu Asp Phe Thr Trp Glu Lys Pro Pro Glu Asp Pro Pro Asp Ser Lys
        195                 200                 205

Asn
```

<210> SEQ ID NO 7
<211> LENGTH: 34
<212> TYPE: PRT
<213> ORGANISM: Artificial Sequence
<220> FEATURE:
<223> OTHER INFORMATION: Human CD80 signal sequence

<400> SEQUENCE: 7

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30
```

Ser Gly

<210> SEQ ID NO 8
<211> LENGTH: 37
<212> TYPE: PRT
<213> ORGANISM: Artificial Sequence
<220> FEATURE:
<223> OTHER INFORMATION: Mouse CD80 signal sequence

<400> SEQUENCE: 8

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp
        35

<210> SEQ ID NO 9
<211> LENGTH: 232
<212> TYPE: PRT
<213> ORGANISM: Artificial Sequence
<220> FEATURE:
<223> OTHER INFORMATION: Fc C237S

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 10

<211> LENGTH: 228
<212> TYPE: PRT
<213> ORGANISM: Artificial Sequence
<220> FEATURE:
<223> OTHER INFORMATION: Fc

<400> SEQUENCE: 10

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 11
<211> LENGTH: 229
<212> TYPE: PRT
<213> ORGANISM: Artificial Sequence
<220> FEATURE:
<223> OTHER INFORMATION: Fc

<400> SEQUENCE: 11

```
Glu Ser Lys Tyr Gly Pro Pro Cys Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
```

```
                85                  90                  95
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 12
<211> LENGTH: 232
<212> TYPE: PRT
<213> ORGANISM: Artificial Sequence
<220> FEATURE:
<223> OTHER INFORMATION: Human IgG1 Fc L234F, L235E, P331S mutant

<400> SEQUENCE: 12

Glu Pro Lys Ser Ser Asp Lys Thr His Thr Cys Pro Pro Cys Pro Ala
1               5                   10                  15

Pro Glu Phe Glu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
```

-continued

```
            210                 215                 220
Ser Leu Ser Leu Ser Pro Gly Lys
225                 230

<210> SEQ ID NO 13
<211> LENGTH: 232
<212> TYPE: PRT
<213> ORGANISM: Artificial Sequence
<220> FEATURE:
<223> OTHER INFORMATION: Human IgG1 Fc N297 mutant

<400> SEQUENCE: 13

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Gly Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 14
<211> LENGTH: 232
<212> TYPE: PRT
<213> ORGANISM: Artificial Sequence
<220> FEATURE:
<223> OTHER INFORMATION: Fc human IgG1

<400> SEQUENCE: 14

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45
```

```
Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 15
<211> LENGTH: 279
<212> TYPE: PRT
<213> ORGANISM: Artificial Sequence
<220> FEATURE:
<223> OTHER INFORMATION: Fc human IgG3

<400> SEQUENCE: 15

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
                20                  25                  30

Glu Pro Lys Ser Cys Asp Thr Pro Pro Cys Pro Arg Cys Pro Glu
            35                  40                  45

Pro Lys Ser Cys Asp Thr Pro Pro Cys Pro Arg Cys Pro Ala Pro
 50                  55                  60

Glu Leu Leu Gly Gly Pro Ser Val Phe Leu Phe Pro Pro Lys Pro Lys
 65                  70                  75                  80

Asp Thr Leu Met Ile Ser Arg Thr Pro Glu Val Thr Cys Val Val Val
                 85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
                115                 120                 125

Asn Ser Thr Phe Arg Val Val Ser Val Leu Thr Val Leu His Gln Asp
130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175
```

-continued

```
Glu Pro Gln Val Tyr Thr Leu Pro Pro Ser Arg Glu Met Thr Lys
                180                 185                 190

Asn Gln Val Ser Leu Thr Cys Leu Val Lys Gly Phe Tyr Pro Ser Asp
            195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
            275

<210> SEQ ID NO 16
<211> LENGTH: 229
<212> TYPE: PRT
<213> ORGANISM: Artificial Sequence
<220> FEATURE:
<223> OTHER INFORMATION: Fc human IgG4

<400> SEQUENCE: 16

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 17
<211> LENGTH: 442
```

```
<212> TYPE: PRT
<213> ORGANISM: Artificial Sequence
<220> FEATURE:
<223> OTHER INFORMATION: Mouse CD80 ECD mouse Fc IgG2a

<400> SEQUENCE: 17
```

| | | | | | | | | | | | | | | |
|---|---|---|---|---|---|---|---|---|---|---|---|---|---|---|
| Val | Asp | Glu | Gln | Leu | Ser | Lys | Ser | Val | Lys | Asp | Lys | Val | Leu | Pro |
| 1 | | | | 5 | | | | | 10 | | | | | 15 |
| Cys | Arg | Tyr | Asn | Ser | Pro | His | Glu | Asp | Glu | Ser | Glu | Asp | Arg | Ile | Tyr |
| | | | 20 | | | | | 25 | | | | | 30 | | |
| Trp | Gln | Lys | His | Asp | Lys | Val | Val | Leu | Ser | Val | Ile | Ala | Gly | Lys | Leu |
| | | | 35 | | | | 40 | | | | | 45 | | | |
| Lys | Val | Trp | Pro | Glu | Tyr | Lys | Asn | Arg | Thr | Leu | Tyr | Asp | Asn | Thr | Thr |
| | 50 | | | | | 55 | | | | | 60 | | | | |
| Tyr | Ser | Leu | Ile | Ile | Leu | Gly | Leu | Val | Leu | Ser | Asp | Arg | Gly | Thr | Tyr |
| 65 | | | | | 70 | | | | | 75 | | | | | 80 |
| Ser | Cys | Val | Val | Gln | Lys | Lys | Glu | Arg | Gly | Thr | Tyr | Glu | Val | Lys | His |
| | | | | 85 | | | | | 90 | | | | | 95 | |
| Leu | Ala | Leu | Val | Lys | Leu | Ser | Ile | Lys | Ala | Asp | Phe | Ser | Thr | Pro | Asn |
| | | | 100 | | | | | 105 | | | | | 110 | | |
| Ile | Thr | Glu | Ser | Gly | Asn | Pro | Ser | Ala | Asp | Thr | Lys | Arg | Ile | Thr | Cys |
| | | 115 | | | | | 120 | | | | | 125 | | | |
| Phe | Ala | Ser | Gly | Gly | Phe | Pro | Lys | Pro | Arg | Phe | Ser | Trp | Leu | Glu | Asn |
| 130 | | | | | 135 | | | | | 140 | | | | | |
| Gly | Arg | Glu | Leu | Pro | Gly | Ile | Asn | Thr | Thr | Ile | Ser | Gln | Asp | Pro | Glu |
| 145 | | | | | 150 | | | | | 155 | | | | | 160 |
| Ser | Glu | Leu | Tyr | Thr | Ile | Ser | Ser | Gln | Leu | Asp | Phe | Asn | Thr | Thr | Arg |
| | | | | 165 | | | | | 170 | | | | | 175 | |
| Asn | His | Thr | Ile | Lys | Cys | Leu | Ile | Lys | Tyr | Gly | Asp | Ala | His | Val | Ser |
| | | | 180 | | | | | 185 | | | | | 190 | | |
| Glu | Asp | Phe | Thr | Trp | Glu | Lys | Pro | Pro | Glu | Asp | Pro | Pro | Asp | Ser | Lys |
| | | | 195 | | | | | 200 | | | | | 205 | | |
| Asn | Glu | Pro | Arg | Gly | Pro | Thr | Ile | Lys | Pro | Cys | Pro | Pro | Cys | Lys | Cys |
| 210 | | | | | 215 | | | | | 220 | | | | | |
| Pro | Ala | Pro | Asn | Leu | Leu | Gly | Gly | Pro | Ser | Val | Phe | Ile | Phe | Pro | Pro |
| 225 | | | | | 230 | | | | | 235 | | | | | 240 |
| Lys | Ile | Lys | Asp | Val | Leu | Met | Ile | Ser | Leu | Ser | Pro | Ile | Val | Thr | Cys |
| | | | | 245 | | | | | 250 | | | | | 255 | |
| Val | Val | Val | Asp | Val | Ser | Glu | Asp | Asp | Pro | Asp | Val | Gln | Ile | Ser | Trp |
| | | | 260 | | | | | 265 | | | | | 270 | | |
| Phe | Val | Asn | Asn | Val | Glu | Val | His | Thr | Ala | Gln | Thr | Gln | Thr | His | Arg |
| | | 275 | | | | | 280 | | | | | 285 | | | |
| Glu | Asp | Tyr | Asn | Ser | Thr | Leu | Arg | Val | Val | Ser | Ala | Leu | Pro | Ile | Gln |
| | 290 | | | | | 295 | | | | | 300 | | | | |
| His | Gln | Asp | Trp | Met | Ser | Gly | Lys | Glu | Phe | Lys | Cys | Lys | Val | Asn | Asn |
| 305 | | | | | 310 | | | | | 315 | | | | | 320 |
| Lys | Asp | Leu | Pro | Ala | Pro | Ile | Glu | Arg | Thr | Ile | Ser | Lys | Pro | Lys | Gly |
| | | | | 325 | | | | | 330 | | | | | 335 | |
| Ser | Val | Arg | Ala | Pro | Gln | Val | Tyr | Val | Leu | Pro | Pro | Glu | Glu | Glu |
| | | | 340 | | | | | 345 | | | | | 350 | |
| Met | Thr | Lys | Lys | Gln | Val | Thr | Leu | Thr | Cys | Met | Val | Thr | Asp | Phe | Met |
| | | | 355 | | | | | 360 | | | | | 365 | | |
| Pro | Glu | Asp | Ile | Tyr | Val | Glu | Trp | Thr | Asn | Asn | Gly | Lys | Thr | Glu | Leu |
| | 370 | | | | | 375 | | | | | 380 | | | | |

```
Asn Tyr Lys Asn Thr Glu Pro Val Leu Asp Ser Asp Gly Ser Tyr Phe
385                 390                 395                 400

Met Tyr Ser Lys Leu Arg Val Glu Lys Lys Asn Trp Val Glu Arg Asn
            405                 410                 415

Ser Tyr Ser Cys Ser Val Val His Glu Gly Leu His Asn His His Thr
            420                 425                 430

Thr Lys Ser Phe Ser Arg Thr Pro Gly Lys
            435                 440

<210> SEQ ID NO 18
<211> LENGTH: 441
<212> TYPE: PRT
<213> ORGANISM: Artificial Sequence
<220> FEATURE:
<223> OTHER INFORMATION: Mouse CD80 ECD Human Fc IgG1 WT

<400> SEQUENCE: 18

Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
            85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
            165                 170                 175

Asn His Thr Ile Lys Cys Leu Ile Lys Tyr Gly Asp Ala His Val Ser
            180                 185                 190

Glu Asp Phe Thr Trp Glu Lys Pro Glu Asp Pro Asp Asp Ser Lys
        195                 200                 205

Asn Glu Pro Lys Ser Ser Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
    290                 295                 300
```

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
            325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
            355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
            435                 440

<210> SEQ ID NO 19
<211> LENGTH: 441
<212> TYPE: PRT
<213> ORGANISM: Artificial Sequence
<220> FEATURE:
<223> OTHER INFORMATION: Mouse CD80 ECD Fc IgG1 MT (234, 235, 331)

<400> SEQUENCE: 19

Val Asp Glu Gln Leu Ser Lys Ser Val Lys Asp Lys Val Leu Leu Pro
1               5                   10                  15

Cys Arg Tyr Asn Ser Pro His Glu Asp Glu Ser Glu Asp Arg Ile Tyr
            20                  25                  30

Trp Gln Lys His Asp Lys Val Val Leu Ser Val Ile Ala Gly Lys Leu
        35                  40                  45

Lys Val Trp Pro Glu Tyr Lys Asn Arg Thr Leu Tyr Asp Asn Thr Thr
50                  55                  60

Tyr Ser Leu Ile Ile Leu Gly Leu Val Leu Ser Asp Arg Gly Thr Tyr
65                  70                  75                  80

Ser Cys Val Val Gln Lys Lys Glu Arg Gly Thr Tyr Glu Val Lys His
                85                  90                  95

Leu Ala Leu Val Lys Leu Ser Ile Lys Ala Asp Phe Ser Thr Pro Asn
            100                 105                 110

Ile Thr Glu Ser Gly Asn Pro Ser Ala Asp Thr Lys Arg Ile Thr Cys
        115                 120                 125

Phe Ala Ser Gly Gly Phe Pro Lys Pro Arg Phe Ser Trp Leu Glu Asn
130                 135                 140

Gly Arg Glu Leu Pro Gly Ile Asn Thr Thr Ile Ser Gln Asp Pro Glu
145                 150                 155                 160

Ser Glu Leu Tyr Thr Ile Ser Ser Gln Leu Asp Phe Asn Thr Thr Arg
                165                 170                 175

Asn His Thr Ile Lys Cys Leu Ile Lys Tyr Gly Asp Ala His Val Ser
            180                 185                 190

Glu Asp Phe Thr Trp Glu Lys Pro Pro Glu Asp Pro Pro Asp Ser Lys
        195                 200                 205

Asn Glu Pro Lys Ser Ser Asp Lys Thr His Thr Cys Pro Pro Cys Pro
210                 215                 220

```
Ala Pro Glu Phe Glu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
            245                 250                 255

Val Val Asp Val Ser His Glu Asp Pro Glu Val Lys Phe Asn Trp Tyr
        260                 265                 270

Val Asp Gly Val Glu Val His Asn Ala Lys Thr Lys Pro Arg Glu Glu
    275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Ser Ile Glu Lys Thr Ile Ser Lys Ala Lys Gly Gln
            325                 330                 335

Pro Arg Glu Pro Gln Val Tyr Thr Leu Pro Pro Ser Arg Asp Glu Leu
        340                 345                 350

Thr Lys Asn Gln Val Ser Leu Thr Cys Leu Val Lys Gly Phe Tyr Pro
    355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
            405                 410                 415

Phe Ser Cys Ser Val Met His Glu Ala Leu His Asn His Tyr Thr Gln
        420                 425                 430

Lys Ser Leu Ser Leu Ser Pro Gly Lys
            435                 440

<210> SEQ ID NO 20
<211> LENGTH: 440
<212> TYPE: PRT
<213> ORGANISM: Artificial Sequence
<220> FEATURE:
<223> OTHER INFORMATION: Human CD80 ECD Human Fc IgG1 WT

<400> SEQUENCE: 20

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
                85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140
```

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Glu Pro Lys Ser Ser Asp Lys Thr His Thr Cys Pro Pro Cys Pro Ala
210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
                325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys
        435                 440

<210> SEQ ID NO 21
<211> LENGTH: 440
<212> TYPE: PRT
<213> ORGANISM: Artificial Sequence
<220> FEATURE:
<223> OTHER INFORMATION: Human CD80 ECD Human Fc IgG1 L234F, L235E,
      P331S MT

<400> SEQUENCE: 21

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
                20                  25                  30

Gln Lys Glu Lys Lys Met Val Leu Thr Met Met Ser Gly Asp Met Asn
            35                  40                  45

Ile Trp Pro Glu Tyr Lys Asn Arg Thr Ile Phe Asp Ile Thr Asn Asn
        50                  55                  60

```
Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                 85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205

Glu Pro Lys Ser Ser Asp Lys Thr His Thr Cys Pro Pro Cys Pro Ala
210                 215                 220

Pro Glu Phe Glu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
        275                 280                 285

Tyr Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Ala
305                 310                 315                 320

Leu Pro Ala Ser Ile Glu Lys Thr Ile Ser Lys Ala Lys Gly Gln Pro
                325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys
        435                 440

<210> SEQ ID NO 22
<211> LENGTH: 288
<212> TYPE: PRT
<213> ORGANISM: Artificial Sequence
<220> FEATURE:
```

<223> OTHER INFORMATION: human PD-1 precursor (with signal sequence)
UniProtKB/Swiss-Prot: Q15116.3, 01-OCT-2014

<400> SEQUENCE: 22

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 23
<211> LENGTH: 268
<212> TYPE: PRT
<213> ORGANISM: Artificial Sequence
<220> FEATURE:
<223> OTHER INFORMATION: human PD-1 (mature, without signal sequence)

<400> SEQUENCE: 23

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu

```
                    50                  55                  60
Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Arg Asn
                     85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
            115                 120                 125

Ala Glu Val Pro Thr Ala His Pro Ser Pro Ser Pro Arg Pro Ala Gly
        130                 135                 140

Gln Phe Gln Thr Leu Val Val Gly Val Val Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
                180                 185                 190

Pro Ser Ala Val Pro Val Phe Ser Val Asp Tyr Gly Glu Leu Asp Phe
            195                 200                 205

Gln Trp Arg Glu Lys Thr Pro Glu Pro Pro Val Pro Cys Val Pro Glu
        210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
                260                 265

<210> SEQ ID NO 24
<211> LENGTH: 290
<212> TYPE: PRT
<213> ORGANISM: Artificial Sequence
<220> FEATURE:
<223> OTHER INFORMATION: human PD-L1 precursor (with signal sequence)
      UniProtKB/Swiss-Prot: Q9NZQ7.1, 01-OCT-2014

<400> SEQUENCE: 24

Met Arg Ile Phe Ala Val Phe Ile Phe Met Thr Tyr Trp His Leu Leu
 1                   5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140
```

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 25
<211> LENGTH: 272
<212> TYPE: PRT
<213> ORGANISM: Artificial Sequence
<220> FEATURE:
<223> OTHER INFORMATION: human PD-L1 (mature, without signal sequence)

<400> SEQUENCE: 25

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
            85                  90                  95

Met Ile Ser Tyr Gly Gly Ala Asp Tyr Lys Arg Ile Thr Val Lys Val
        100                 105                 110

Asn Ala Pro Tyr Asn Lys Ile Asn Gln Arg Ile Leu Val Val Asp Pro
    115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
            165                 170                 175

Ser Thr Leu Arg Ile Asn Thr Thr Thr Asn Glu Ile Phe Tyr Cys Thr
        180                 185                 190

Phe Arg Arg Leu Asp Pro Glu Glu Asn His Thr Ala Glu Leu Val Ile
    195                 200                 205

-continued

```
Pro Glu Leu Pro Leu Ala His Pro Pro Asn Glu Arg Thr His Leu Val
    210                 215                 220
Ile Leu Gly Ala Ile Leu Leu Cys Leu Gly Val Ala Leu Thr Phe Ile
225                 230                 235                 240
Phe Arg Leu Arg Lys Gly Arg Met Met Asp Val Lys Lys Cys Gly Ile
                245                 250                 255
Gln Asp Thr Asn Ser Lys Lys Gln Ser Asp Thr His Leu Glu Glu Thr
                260                 265                 270
```